US011739333B2

(12) United States Patent
Guo

(10) Patent No.: US 11,739,333 B2
(45) Date of Patent: Aug. 29, 2023

(54) REGULATION OF GENE EXPRESSION BY APTAMER-MODULATED RNASE P CLEAVAGE

(71) Applicant: MeiraGTx UK II Limited, London (GB)

(72) Inventor: Xuecui Guo, Cold Spring Harbor, NY (US)

(73) Assignee: MEIRAGTX UK II LIMITED, London (GB)

( * ) Notice: Subject to any disclaimer, the term of this patent is extended or adjusted under 35 U.S.C. 154(b) by 372 days.

(21) Appl. No.: 16/487,587

(22) PCT Filed: Mar. 2, 2018

(86) PCT No.: PCT/US2018/020795
§ 371 (c)(1),
(2) Date: Aug. 21, 2019

(87) PCT Pub. No.: WO2018/161053
PCT Pub. Date: Sep. 7, 2018

(65) Prior Publication Data
US 2020/0056182 A1 Feb. 20, 2020

Related U.S. Application Data

(60) Provisional application No. 62/466,138, filed on Mar. 2, 2017.

(51) Int. Cl.
*C12N 15/115* (2010.01)
*C12N 15/11* (2006.01)
*C12N 15/67* (2006.01)

(52) U.S. Cl.
CPC .......... *C12N 15/115* (2013.01); *C12N 15/111* (2013.01); *C12N 15/67* (2013.01); *C12N 2310/126* (2013.01); *C12N 2310/16* (2013.01); *C12N 2310/3519* (2013.01); *C12N 2310/531* (2013.01)

(58) Field of Classification Search
CPC ............ C12N 15/115; C12N 2310/126; C12N 2310/16; C12N 2310/3519; C12N 2310/531
See application file for complete search history.

(56) References Cited

U.S. PATENT DOCUMENTS

2015/0315574 A1   11/2015   Wilusz et al.

FOREIGN PATENT DOCUMENTS

WO       2016/126747 A1     8/2016

OTHER PUBLICATIONS

Li et al (Proc. Nat. Acad. Sci. USA 100(23): 13213-13218, 2003) (Year: 2003).*
Altman et al (Proc. Nat. Acad. Sci. USA 102(32): 11284-11289, 2005) (Year: 2005).*
Perdrizet et al (Proc. Nat. Acad. Sci. USA 109(9): 3323-3328) (Year: 2012).*
Wieland, M., "Design of Artificial, Ribozyme-Based Genetic Switches in Bacteria"; Dissertation, University of Konstanz (2010); 99 pgs.
Saragliadis, A., "Conditional Gene Expression Using Ribozymes; Post-Transcriptional Control Amino Acid Identity in Protein Synthesis and Temperature-Dependent Gene Expression"; Dissertation, University of Konstanz (2013); 98 pgs.
Ogawa, A. et al., "An Artificial Aptazyme-Based Riboswitch and its Cascading System in *E. Coli*"; Chem. Bio. Chem. (2008); vol. 9, pp. 206-209.

* cited by examiner

*Primary Examiner* — Richard A Schnizer
(74) *Attorney, Agent, or Firm* — Fox Rothschild LLP

(57) ABSTRACT

The present disclosure provides polynucleotide constructs for the modulation of target gene expression by aptamer-mediated ribonuclease cleavage of the target gene RNA and methods of using the constructs to modulate gene expression in response to the presence or absence of a ligand that binds the aptamer. The polynucleotide constructs contains a ribonuclease substrate sequence (e.g., an RNase P substrate) and a riboswitch comprising an effector region and an aptamer such that when the aptamer binds a ligand, target gene expression occurs.

25 Claims, 13 Drawing Sheets

Specification includes a Sequence Listing.

Mutation in T-loop

MG1 construct

GM1 construct

MG1 (SEQ ID NO: 1):

CCTCATAAAGGCCAAGAAGGGCGGAAAGATCGCCGTGTAAggatccaagacgagctgtacaa gtaaagcggccaattcggacaaaaacgagacgctggtggctggcactcctggtttccaggacggggttcaagtccctgcggtgtcataatcgcgtggatatggcacgcaagtttctaccgggcaccgtaaatgtccgactagacaccatctagagtcgacctgcaggcatgcaa gcttcagctgctcgagggcccagatctaattcaccccaccagtgcaggctgcctatcag

GM1 (SEQ ID NO: 2):

CCTCATAAAGGCCAAGAAGGGCGGAAAGATCGCCGTGTAAggatccaagacgagctgtacaa gtaaagcggccgtaatgtataatcgcgtggatatggcacgcaagtttctaccgggcaccgtaaatgtccgactacattagacgctggtggctggcactcctggtttccaggacggggttcaagtccctgcggtgtcttgcttggatcggccgcgactctagagtcgacctgcagg catgcaagcttcagctgctcgagggcccagatctaattcaccccaccagtgcaggctgcctatcag

GM2 (SEQ ID NO: 3):

CCTCATAAAGGCCAAGAAGGGCGGAAAGATCGCCGTGTAAggatccaagacgagctgtacaa gtaaagcggcccgatcatataatcgcgtggatatggcacgcaagtttctaccgggcaccgtaaatgtccgactatggtgacgctggtggctggcactcctggtttccaggacggggttcaagtccctgcggtgtcttgcttggatcggccgcgactctagagtcgacctgcagg catgcaagcttcagctgctcgagggcccagatctaattcaccccaccagtgcaggctgcctatcag

GM3 (SEQ ID NO: 4):

CCTCATAAAGGCCAAGAAGGGCGGAAAGATCGCCGTGTAAggatccaagacgagctgtacaa gtaaagcggccggacaaaataatcgcgtggatatggcacgcaagtttctaccgggcaccgtaaatgtccgacttttgtccaacgagacgctggtggctggcactcctggtttccaggacggggttcaagtccctgcggtgtcttgcttggatcggccgcgactctagagtcgacct gcaggcatgcaagcttcagctgctcgagggcccagatctaattcaccccaccagtgcaggctgcctatcag

GM4 (SEQ ID NO: 5):

CCTCATAAAGGCCAAGAAGGGCGGAAAGATCGCCGTGTAAggatccaagacgagctgtacaa gtaaagaagacgtaatgtataatcgcgtggatatggcacgcaagtttctaccgggcaccgtaaatgtccgactacattagacgctggtggctggcactcctggtttccaggacggggttcaagtccctgcggtgtcttgcttggatcggccgcgactctagagtcgacctgcagg catgcaagcttcagctgctcgagggcccagatctaattcaccccaccagtgcaggctgcctatcag

Fig. 8

GM4_2C (SEQ ID NO: 6):

CCTCATAAAGGCCAAGAAGGGCGGAAAGATCGCCGTGTAAggatccaagacgagctgtacaa
gtaaagaagacgtaatgtataatcgcgtggatatggcacgcaagtttctaccgggcaccgtaaatgtccgactacattagcgacgctggt
ggctggcactcctggtttccaggacggggttcaagtccctgcggtgtcttgcttggatcggccgcgactctagagtcgacctgcagg
catgcaagcttcagaagtaaagaagacgtaatgtataatcgcgtggatatggcacgcaagtttctaccgggcaccgtaaatgtccgact
acattagcgacgctggtggctggcactcctggtttccaggacggggttcaagtccctgcggtgtcttgcttggatcggccgcgactcta
gagtcgacctgcaggcatgcaagcttcagctgctcgagggcccagatctaattcaccccaccagtgcaggctgcctatcag

GM5 (SEQ ID NO: 7):

CCTCATAAAGGCCAAGAAGGGCGGAAAGATCGCCGTGTAAggatcCAAGACGAGC
TGTACAAGTAAAGaagagctaatgtataatcgcgtggatatggcacgcaagtttctaccgggcaccgtaaatgtccgacta
cattagcgacgctggtggctggcactcctggtttccaggacggggttcaagtccctgcggtgtcttgcttggatcggccgcgactcta
gagtcgacctgcaggcatgcaagcttcagctgctcgagggcccagatctaattcaccccaccagtgcaggctgcctatcag

GM6 (SEQ ID NO: 8):

CCTCATAAAGGCCAAGAAGGGCGGAAAGATCGCCGTGTAAggatccaagacgagctgtacaa
gtaaagaagagctaatgtataatcgcgtggatatggcacgcaagtttctaccgggcaccgtaaatgtccgactacattagcagacgctg
gtggctggcactcctggtttccaggacggggttcaagtccctgcggtgtcttgcttggatcggccgcgactctagagtcgacctgca
ggcatgcaagcttcagctgctcgagggcccagatctaattcaccccaccagtgcaggctgcctatcag

GM7 (SEQ ID NO: 9):

CCTCATAAAGGCCAAGAAGGGCGGAAAGATCGCCGTGTAAggatccaagacgagctgtacaa
gtaaagaagagctaatgtataatcgcgtggatatggcacgcaagtttctaccgggcaccgtaaatgtccgactacattagcgagacgct
ggtggctggcactcctggtttccaggacggggttcaagtccctgcggtgtcttgcttggatcggccgcgactctagagtcgacctgc
aggcatgcaagcttcagctgctcgagggcccagatctaattcaccccaccagtgcaggctgcctatcag

GM8 (SEQ ID NO: 10):

CCTCATAAAGGCCAAGAAGGGCGGAAAGATCGCCGTGTAAggatccaagacgagctgtacaa
gtaaagaagagctaatgtataatcgcgtggatatggcacgcaagtttctaccgggcaccgtaaatgtccgactacattagccgagacg
ctggtggctggcactcctggtttccaggacggggttcaagtccctgcggtgtcttgcttggatcggccgcgactctagagtcgacctg
caggcatgcaagcttcagctgctcgagggcccagatctaattcaccccaccagtgcaggctgcctatcag

Fig. 8 (Cont.)

MG2 (SEQ ID NO: 11):

CCTCATAAAGGCCAAGAAGGGCGGAAAGATCGCCGTGTAAggatccaagacgagctgtacaa
gtaaagcggccaattcggacaaaaacga*gacgctggtggctggcactcctggtttccaggacggggttcaagtccctgcggtgtc*t
ataatcgcgtggatatggcacgcaagtttctaccgggcaccgtaaatgtccgactaagacacatctagagtcgacctgcaggcatgca
agcttcagctgctcgagggcccagatctaattcacccaccagtgcaggctgcctatcag

MG3 (SEQ ID NO: 12):

CCTCATAAAGGCCAAGAAGGGCGGAAAGATCGCCGTGTAAggatccaagacgagctgtacaa
gtaaagcggccaattcggacaaaaacga*gacgctggtggctggcactcctggtttccaggacggggttcaagtccctgcggtgtc*g
tataatcgcgtggatatggcacgcaagtttctaccgggcaccgtaaatgtccgactacagacaatctagagtcgacctgcaggcatgca
agcttcagctgctcgagggcccagatctaattcacccaccagtgcaggctgcctatcag

MG4 (SEQ ID NO: 13):

CCTCATAAAGGCCAAGAAGGGCGGAAAGATCGCCGTGTAAggatcCAAGACGAGC
TGTACAAGTAAAGCGGCCaattCGGACAAAAACGA*gacgctggtggctggcactcctggtttccagga*
*cggggttcaagtccctgcggtgtc*agtataatcgcgtggatatggcacgcaagtttctaccgggcaccgtaaatgtccgactactaga
cttctagagtcgacctgcaggcatgcaagcttcagctgctcgagggcccagatctaattcacccaccagtgcaggctgcctatcag GArg (SEQ ID NO: 14):

CCTCATAAAGGCCAAGAAGGGCGGAAAGATCGCCGTGTAAggatccaAgacgagctgtaca
agtaaagaagactgcgacgataatcgcgtggatatggcacgcaagtttctaccgggcaccgtaaatgtccgactcgtcgca*gggcca*
*ctggccgcaatggataacgcgtctgactacggatcagatgattccaggttcgactcctggctggctg*ggtgtaggccgcgactctag
agtcgacctgcaggcatgcaagcttcagctgctcgagggcccagatctaattcacccaccagtgcaggctgcctatcag

YM (SEQ ID NO: 15):

CCTCATAAAGGCCAAGAAGGGCGGAAAGATCGCCGTGTAAggatcCAAGACGAGC
TGTACAAGTAAAGCGGCcgtaatgttataacctcaataatatggtttgaggggtgtctaccaggaaccgtaaaatcctgatt
aacatta*gacgctggtggctggcactcctggtttccaggacggggttcaagtccctgcggtgtc*ttgcttggatcggccgcgactct
agagtcgacctgcaggcatgcaagcttcagctgctcgagggcccagatctaattcacccaccagtgcaggctgcctatcag

Fig. 8 (Cont.)

TheoM (SEQ ID NO: 16):

CCTCATAAAGGCCAAGAAGGGCGGAAAGATCGCCGTGTAAggatcCAAGACGAGC
TGTACAAGTAAAGCGGCctaatgtgataccagccgaaaggcccttggcagcacattagacgctggtggctggcactc
ctggttccaggacggggttcaagtccctgcggtgtcttgcttggatcggccgcgactctagagtcgacctgcaggcatgcaagcttc
agctgctcgagggcccagatctaattcaccccaccagtgcaggctgcctatcag

Fig. 8 (Cont.)

SEQUENCE LISTING

<160> NUMBER OF SEQ ID NOS: 19

<210> SEQ ID NO 1
<211> LENGTH: 296
<212> TYPE: DNA
<213> ORGANISM: Artificial Sequence
<220> FEATURE:
<223> OTHER INFORMATION: Synthetic construct

<400> SEQUENCE: 1

```
cctcataaag gccaagaagg gcggaaagat cgccgtgtaa ggatccaaga cgagctgtac      60
aagtaaagcg gccaattcgg acaaaaacga gacgctggtg gctggcactc ctggtttcca     120
ggacggggtt caagtccctg cggtgtctat aatcgcgtgg atatggcacg caagtttcta     180
ccgggcaccg taaatgtccg actagacacc atctagagtc gacctgcagg catgcaagct     240
tcagctgctc gagggcccag atctaattca ccccaccagt gcaggctgcc tatcag        296
```

<210> SEQ ID NO 2
<211> LENGTH: 305
<212> TYPE: DNA
<213> ORGANISM: Artificial Sequence
<220> FEATURE:
<223> OTHER INFORMATION: Synthetic construct

<400> SEQUENCE: 2

```
cctcataaag gccaagaagg gcggaaagat cgccgtgtaa ggatccaaga cgagctgtac      60
```

| | |
|---|---|
| aagtaaagcg gccgtaatgt ataatcgcgt ggatatggca cgcaagtttc taccgggcac | 120 |
| cgtaaatgtc cgactacatt acgacgctgg tggctggcac tcctggtttc caggacgggg | 180 |
| ttcaagtccc tgcggtgtct tgcttggat cggccgcgac tctagagtcg acctgcaggc | 240 |
| atgcaagctt cagctgctcg agggcccaga tctaattcac cccaccagtg caggctgcct | 300 |
| atcag | 305 |

```
<210> SEQ ID NO 3
<211> LENGTH: 304
<212> TYPE: DNA
<213> ORGANISM: Artificial Sequence
<220> FEATURE:
<223> OTHER INFORMATION: Synthetic construct

<400> SEQUENCE: 3
```

| | |
|---|---|
| cctcataaag gccaagaagg gcggaaagat cgccgtgtaa ggatccaaga cgagctgtac | 60 |
| aagtaaagcg gcccgatcat ataatcgcgt ggatatggca cgcaagtttc taccgggcac | 120 |
| cgtaaatgtc cgactatggt cgacgctggt ggctggcact cctggtttcc aggacggggt | 180 |
| tcaagtccct gcggtgtctt gcttggatc ggccgcgact ctagagtcga cctgcaggca | 240 |
| tgcaagcttc agctgctcga gggcccagat ctaattcacc ccaccagtgc aggctgccta | 300 |
| tcag | 304 |

```
<210> SEQ ID NO 4
<211> LENGTH: 310
<212> TYPE: DNA
<213> ORGANISM: Artificial Sequence
<220> FEATURE:
<223> OTHER INFORMATION: Synthetic construct

<400> SEQUENCE: 4
```

| | |
|---|---|
| cctcataaag gccaagaagg gcggaaagat cgccgtgtaa ggatccaaga cgagctgtac | 60 |
| aagtaaagcg gccggacaaa ataatcgcgt ggatatggca cgcaagtttc taccgggcac | 120 |
| cgtaaatgtc cgacttttgt ccaacgagac gctggtggct ggcactcctg gtttccagga | 180 |
| cggggttcaa gtccctgcgg tgtctttgct tggatcggcc gcgactctag agtcgacctg | 240 |
| caggcatgca agcttcagct gctcgagggc ccagatctaa ttccccccac cagtgcaggc | 300 |
| tgcctatcag | 310 |

```
<210> SEQ ID NO 5
<211> LENGTH: 305
<212> TYPE: DNA
<213> ORGANISM: Artificial Sequence
<220> FEATURE:
<223> OTHER INFORMATION: Synthetic construct

<400> SEQUENCE: 5
```

| | |
|---|---|
| cctcataaag gccaagaagg gcggaaagat cgccgtgtaa ggatccaaga cgagctgtac | 60 |
| aagtaaagaa gacgtaatgt ataatcgcgt ggatatggca cgcaagtttc taccgggcac | 120 |
| cgtaaatgtc cgactacatt acgacgctgg tggctggcac tcctggtttc caggacgggg | 180 |
| ttcaagtccc tgcggtgtct tgcttggat cggccgcgac tctagagtcg acctgcaggc | 240 |
| atgcaagctt cagctgctcg agggcccaga tctaattcac cccaccagtg caggctgcct | 300 |
| atcag | 305 |

```
<210> SEQ ID NO 6
<211> LENGTH: 498
```

<212> TYPE: DNA
<213> ORGANISM: Artificial Sequence
<220> FEATURE:
<223> OTHER INFORMATION: Synthetic construct

<400> SEQUENCE: 6

```
cctcataaag gccaagaagg gcggaaagat cgccgtgtaa ggatccaaga cgagctgtac      60
aagtaaagaa gacgtaatgt ataatcgcgt ggatatggca cgcaagtttc taccgggcac     120
cgtaaatgtc cgactacatt acgacgctgg tggctggcac tcctggtttc aggacgggg     180 ttcaagtccc tgcggtgtct ttgcttggat cggccgcgac tctagagtcg acctgcaggc     240
atgcaagctt cagaagtaaa gaagacgtaa tgtataatcg cgtggatatg gcacgcaagt     300
ttctaccggg caccgtaaat gtccgactac attacgacgc tggtggctgg cactcctggt     360
ttccaggacg gggttcaagt ccctgcggtg tctttgcttg gatcggccgc gactctagag     420
tcgacctgca ggcatgcaag cttcagctgc tcgagggccc agatctaatt caccccacca     480
gtgcaggctg cctatcag                                                   498
```

<210> SEQ ID NO 7
<211> LENGTH: 306
<212> TYPE: DNA
<213> ORGANISM: Artificial Sequence
<220> FEATURE:
<223> OTHER INFORMATION: Synthetic construct

<400> SEQUENCE: 7

```
cctcataaag gccaagaagg gcggaaagat cgccgtgtaa ggatccaaga cgagctgtac      60
aagtaaagaa gagctaatgt ataatcgcgt ggatatggca cgcaagtttc taccgggcac     120
cgtaaatgtc cgactacatt agcgacgctg gtggctggca ctcctggttt ccaggacggg     180
gttcaagtcc ctgcggtgtc tttgcttgga tcggccgcga ctctagagtc gacctgcagg     240
catgcaagct tcagctgctc gagggcccag atctaattca ccccaccagt gcaggctgcc     300
tatcag                                                                306
```

<210> SEQ ID NO 8
<211> LENGTH: 307
<212> TYPE: DNA
<213> ORGANISM: Artificial Sequence
<220> FEATURE:
<223> OTHER INFORMATION: Synthetic construct

<400> SEQUENCE: 8

```
cctcataaag gccaagaagg gcggaaagat cgccgtgtaa ggatccaaga cgagctgtac      60
aagtaaagaa gagctaatgt ataatcgcgt ggatatggca cgcaagtttc taccgggcac     120
cgtaaatgtc cgactacatt agcagacgct ggtggctggc actcctggtt tccaggacgg     180
ggttcaagtc cctgcggtgt ctttgcttgg atcggccgcg actctagagt cgacctgcag     240
gcatgcaagc ttcagctgct cgagggccca gatctaattc accccaccag tgcaggctgc     300
ctatcag                                                               307
```

<210> SEQ ID NO 9
<211> LENGTH: 308
<212> TYPE: DNA
<213> ORGANISM: Artificial Sequence
<220> FEATURE:
<223> OTHER INFORMATION: Synthetic construct

<400> SEQUENCE: 9

```
cctcataaag gccaagaagg gcggaaagat cgccgtgtaa ggatccaaga cgagctgtac      60
aagtaaagaa gagctaatgt ataatcgcgt ggatatggca cgcaagtttc taccgggcac     120
cgtaaatgtc cgactacatt agcgagacgc tggtggctgg cactcctggt ttccaggacg     180
gggttcaagt ccctgcggtg tctttgcttg gatcggccgc gactctagag tcgacctgca     240
ggcatgcaag cttcagctgc tcgagggccc agatctaatt caccccacca gtgcaggctg     300
cctatcag                                                              308
```

```
<210> SEQ ID NO 10
<211> LENGTH: 309
<212> TYPE: DNA
<213> ORGANISM: Artificial Sequence
<220> FEATURE:
<223> OTHER INFORMATION: Synthetic construct

<400> SEQUENCE: 10
cctcataaag gccaagaagg gcggaaagat cgccgtgtaa ggatccaaga cgagctgtac      60
aagtaaagaa gagctaatgt ataatcgcgt ggatatggca cgcaagtttc taccgggcac     120
cgtaaatgtc cgactacatt agccgagacg ctggtggctg gcactcctgg tttccaggac     180
ggggttcaag tccctgcggt gtctttgctt ggatcggccg cgactctaga gtcgacctgc     240
aggcatgcaa gcttcagctg ctcgagggcc cagatctaat tcaccccacc agtgcaggct     300
gcctatcag                                                             309
```

```
<210> SEQ ID NO 11
<211> LENGTH: 297
<212> TYPE: DNA
<213> ORGANISM: Artificial Sequence
<220> FEATURE:
<223> OTHER INFORMATION: Synthetic construct

<400> SEQUENCE: 11
cctcataaag gccaagaagg gcggaaagat cgccgtgtaa ggatccaaga cgagctgtac      60
aagtaaagcg gccaattcgg acaaaaacga gacgctggtg gctggcactc ctggtttcca     120
ggacggggtt caagtccctg cggtgtctta taatcgcgtg gatatggcac gcaagtttct     180
accgggcacc gtaaatgtcc gactaagaca catctagagt cgacctgcag gcatgcaagc     240
ttcagctgct cgagggccca gatctaattc accccaccag tgcaggctgc ctatcag       297
```

```
<210> SEQ ID NO 12
<211> LENGTH: 298
<212> TYPE: DNA
<213> ORGANISM: Artificial Sequence
<220> FEATURE:
<223> OTHER INFORMATION: Synthetic construct

<400> SEQUENCE: 12
cctcataaag gccaagaagg gcggaaagat cgccgtgtaa ggatccaaga cgagctgtac      60
aagtaaagcg gccaattcgg acaaaaacga gacgctggtg gctggcactc ctggtttcca     120
ggacggggtt caagtccctg cggtgtctgt ataatcgcgt ggatatggca cgcaagtttc     180
taccgggcac cgtaaatgtc cgactacaga caatctagag tcgacctgca ggcatgcaag     240
cttcagctgc tcgagggccc agatctaatt caccccacca gtgcaggctg cctatcag      298
```

```
<210> SEQ ID NO 13
<211> LENGTH: 299
<212> TYPE: DNA
<213> ORGANISM: Artificial Sequence
```

<220> FEATURE:
<223> OTHER INFORMATION: Synthetic construct

<400> SEQUENCE: 13

```
cctcataaag gccaagaagg gcggaaagat cgccgtgtaa ggatccaaga cgagctgtac      60
aagtaaagcg gccaattcgg acaaaaacga gacgctggtg gctggcactc ctggtttcca     120
ggacggggtt caagtccctg cggtgtctag tataatcgcg tggatatggc acgcaagttt     180
ctaccgggca ccgtaaatgt ccgactacta gacttctaga gtcgacctgc aggcatgcaa     240
gcttcagctg ctcgagggcc cagatctaat tcaccccacc agtgcaggct gcctatcag     299
```

<210> SEQ ID NO 14
<211> LENGTH: 314
<212> TYPE: DNA
<213> ORGANISM: Artificial Sequence
<220> FEATURE:
<223> OTHER INFORMATION: Synthetic construct

<400> SEQUENCE: 14

```
cctcataaag gccaagaagg gcggaaagat cgccgtgtaa ggatccaaga cgagctgtac      60
aagtaaagaa gactgcgacg ataatcgcgt ggatatggca cgcaagtttc taccgggcac     120
cgtaaatgtc cgactcgtcg cagggccagt ggcgcaatgg ataacgcgtc tgactacgga     180
tcagaagatt ccaggttcga ctcctggctg gctcggtgta ggccgcgact ctagagtcga     240
cctgcaggca tgcaagcttc agctgctcga gggcccagat ctaattcacc ccaccagtgc     300
aggctgccta tcag                                                        314
```

<210> SEQ ID NO 15
<211> LENGTH: 307
<212> TYPE: DNA
<213> ORGANISM: Artificial Sequence
<220> FEATURE:
<223> OTHER INFORMATION: Synthetic construct

<400> SEQUENCE: 15

```
cctcataaag gccaagaagg gcggaaagat cgccgtgtaa ggatccaaga cgagctgtac      60
aagtaaagcg gccgtaatgt tataacctca ataatatggt ttgagggtgt ctaccaggaa     120
ccgtaaaatc ctgattaaca ttacgacgct ggtggctggc actcctggtt tccaggacgg     180
ggttcaagtc cctgcggtgt ctttgcttgg atcggccgcg actctagagt cgacctgcag     240
gcatgcaagc ttcagctgct cgagggccca gatctaattc accccaccag tgcaggctgc     300
ctatcag                                                                307
```

<210> SEQ ID NO 16
<211> LENGTH: 275
<212> TYPE: DNA
<213> ORGANISM: Artificial Sequence
<220> FEATURE:
<223> OTHER INFORMATION: Synthetic construct

<400> SEQUENCE: 16

```
cctcataaag gccaagaagg gcggaaagat cgccgtgtaa ggatccaaga cgagctgtac      60
aagtaaagcg gcctaatgtg ataccagccg aaaggcccct tggcagcacat tagacgctgg    120
tggctggcac tcctggtttc caggacgggg ttcaagtccc tgcggtgtct ttgcttggat     180
cggccgcgac tctagagtcg acctgcaggc atgcaagctt cagctgctcg agggcccaga    240
tctaattcac cccaccagtg caggctgcct atcag                                 275
```

```
<210> SEQ ID NO 17
<211> LENGTH: 58
<212> TYPE: RNA
<213> ORGANISM: Artificial Sequence
<220> FEATURE:
<223> OTHER INFORMATION: Mouse mascRNA or mutant mouse mascRNA inserted
      in the 3' UTR of a luciferase gene

<400> SEQUENCE: 17
gacgcuggug gcuggcacuc cugguuucca ggacgggguu caagucccug cgugucu          58

<210> SEQ ID NO 18
<211> LENGTH: 58
<212> TYPE: RNA
<213> ORGANISM: Artificial Sequence
<220> FEATURE:
<223> OTHER INFORMATION: Mutations in the T-loop of the mascRNA
      (Luci-masc-mlp)

<400> SEQUENCE: 18
gacgcuggug gcuggcacuc cugguuucca ggacggggaa gaagucccug cgugucu          58

<210> SEQ ID NO 19
<211> LENGTH: 18
<212> TYPE: DNA
<213> ORGANISM: Artificial Sequence
<220> FEATURE:
<223> OTHER INFORMATION: Locked Nucleic Acid (LNA)-modified
      oligonucleotides

<400> SEQUENCE: 19
tggaaaccag gagtgcca                                                     18
```

REGULATION OF GENE EXPRESSION BY APTAMER-MODULATED RNASE P CLEAVAGE

FIELD OF THE INVENTION

The invention provides polynucleotide constructs for the modulation of gene expression by aptamer-mediated ribonuclease cleavage of the RNA and methods of using the constructs to modulate gene expression in response to the presence or absence of a ligand that binds the aptamer. The polynucleotide construct contains a ribonuclease substrate sequence and a riboswitch comprising an effector region and an aptamer such that when the aptamer binds a ligand, target gene expression occurs.

BACKGROUND OF THE INVENTION

Ribonuclease P ("RNase P") is a ribonucleoprotein complex and functions as an endoribonuclease that removes 5' leader sequences from precursor tRNAs to generate mature tRNAs by catalyzing the hydrolysis of a specific phosphodiester bond. RNase P is found in species across all kingdoms and is made up of one RNA subunit and one (Bacteria) or many (Archaea and Eukarya) proteins. Studies on RNase P substrate recognition have revealed that the enzyme recognizes the structure rather than the primary nucleotide sequence of the substrates, and can cleave a model substrate that contains a structure equivalent to the acceptor stem, the T-stem, the 3' trail sequence and the 5' leader sequence of a precursor tRNA.

RNase P cleavage of a target mRNA has been accomplished by expressing an external guide sequence (EGS), which is a sequence designed to form a hybrid complex with the mRNA target sequence that resembles a precursor tRNA. The EGS binds to its mRNA target through base pairing interactions and guides RNase P cleavage of the mRNA target. Use of an EGS sequence to target RNase P cleavage requires expression of the exogenous EGS sequence.

SUMMARY OF THE INVENTION

In one aspect, the present invention provides a polynucleotide cassette for the regulation of the expression of a target gene comprising an RNase P substrate sequence linked to a riboswitch wherein the riboswitch comprises an effector region and an aptamer, wherein the effector region comprises a sequence complimentary to a portion of the RNase P substrate sequence. In one embodiment, the aptamer binds a small molecule ligand.

In embodiments of the invention, the effector region comprises sequence capable of forming a stem structure upon ligand binding the aptamer wherein the effector region stem is 7 to 12 base pairs. In embodiments of the invention, the effector region stem is 7, 8, 9, 10, 11, or 12 base pairs.

In one embodiment, the RNase P substrate sequence comprises a sequence encoding a precursor tRNA or a homologous sequence. In other embodiments, the RNase P target sequence comprises a sequence encoding a tRNA, mascRNA, MEN beta tRNA-like structure, a viral tRNA-like structure, a RNase P model substrate, and homologous sequences that can initiate RNase P cleavage.

In one embodiment, the aptamer sequence of the polynucleotide cassette is located 5' to the RNase P substrate sequence and the effector region comprises sequence complimentary to the leader sequence of the RNase P substrate. In one embodiment, the aptamer sequence is located 5' to the RNase P substrate sequence and the effector region comprises all or part of the leader sequence and all or part of the 5' acceptor stem sequence of the RNase P substrate sequence. In further embodiments, the acceptor stem of the RNase P substrate and the riboswitch effector region are separated by 0, 1, 2, 3, or 4 nucleotides. In other embodiments, the effector region stem includes, in addition to leader sequence (and its complement), one or more nucleotides of the acceptor stem of the RNase P substrate, and sequence complementary to the one or more nucleotides of the acceptor stem.

In one embodiment, the aptamer sequence of the polynucleotide cassette is located 3' to the RNase P substrate sequence and the effector region comprises sequence complimentary to the all or part of the 3' acceptor stem of the RNase P substrate sequence. In further embodiments, the effector region sequence complimentary to the 3' acceptor stem of the RNase P substrate is 1 to 7 nucleotides. In other words, the effector region stem includes 1 to 7 nucleotides of the acceptor stem and includes sequence that is complementary to this 1 to 7 nucleotides of the acceptor stem.

In one embodiment, the riboswitch is located 3' of the RNase P substrate so the effector region stem and the acceptor stem of the RNase P substrate do not overlap. In embodiments, the effector region and the acceptor stem of the RNase P substrate are immediately adjacent (i.e., not overlapping). In other embodiments, the effector region and the acceptor stem of the RNase P substrate are separated by 1, 2, 3, 4, 5 or more nucleotides.

In one embodiment, the riboswitch sequence is located within a stem-loop of the RNase P substrate sequence. In one embodiment, the riboswitch sequence is located within the D stem-loop of the RNase P substrate sequence. In one embodiment, the riboswitch sequence is located within the T stem-loop of the RNase P substrate sequence. In one embodiment, the riboswitch sequence is located in the variable loop of the RNase P substrate sequence. In one embodiment, the riboswitch sequence is located within the anticodon stem-loop of the RNase P substrate sequence.

In another aspect, the present invention provides a method of modulating the expression of a target gene comprising: (a) inserting the polynucleotide cassette of the present invention into an untranslated region (UTR) of the target gene; (b) introducing the target gene comprising the polynucleotide cassette into a cell, and (c) exposing the cell to a ligand that specifically binds the aptamer in an amount effective to increase expression of the target gene. In one embodiment, the ligand is a small molecule.

In one embodiment, the polynucleotide cassette is inserted into the 5' untranslated region of the target gene. In one embodiment, the polynucleotide cassette is inserted into the 3' untranslated region of the target gene. In one embodiment, the polynucleotide cassette is inserted into an intron of the target gene.

In one embodiment, two or more of the polynucleotide cassettes are inserted into the target gene. In one embodiment, the two or more polynucleotide cassettes comprise different aptamers that specifically bind to different small molecule ligands. In one embodiment, the two or more polynucleotide cassettes comprise the same aptamer. In one embodiment, the two or more polynucleotide cassettes are in the 5' untranslated region of the target gene, the 3' untranslated region, or both.

In one aspect, the polynucleotide cassette of the present invention is used in combination with other mechanisms for the regulation of expression of the target gene. In one embodiment, a polynucleotide cassette of the present invention is used in combination with a gene regulation cassette that modulates target gene expression by aptamer-mediated regulation of alternative splicing as described in WO 2016/126747 (PCT/US2016/016234), incorporated herein by reference. In other embodiments, the polynucleotide cassette of the present invention used in combination with a gene regulation cassette that modulates target gene expression by aptamer-mediated regulation of self-cleaving ribozymes as described in PCT/US2017/016303, incorporated herein by reference. In other embodiments, the polynucleotide cassette of the present invention is used in combination with a gene regulation cassette that modulates target gene expression by aptamer-mediated modulation of polyadenylation as described in PCT/US2017/016279, incorporated herein by reference. In other embodiments, the polynucleotide cassette of the present invention is used in combination with a gene regulation cassette that modulates target gene expression by aptamer-mediated accessibility of polyadenylation signals as described in PCT/US2018/019056, incorporated herein by reference.

In one embodiment, the target gene comprising the polynucleotide cassette is incorporated in a vector for the expression of the target gene. In one embodiment, the vector is a viral vector. In one embodiment, the viral vector is selected from the group consisting of adenoviral vector, adeno-associated virus vector, and lentiviral vector.

In another aspect, the invention provides a vector comprising a target gene that contains a polynucleotide cassette of the present invention. In one embodiment, the vector is a viral vector. In one embodiment, the viral vector is selected from the group consisting of adenoviral vector, adeno-associated virus vector, and lentiviral vector.

In one embodiment, the target gene comprising the polynucleotide cassette is incorporated in an expression construct or vector compromising a non-tissue-specific promoter. In other embodiments, the promoter is tissue specific.

BRIEF DESCRIPTION OF THE FIGURES

FIG. 8. The sequences of the constructs described herein. The 3' end of the target gene (e.g., firefly luciferase) coding sequence is in capital letters; the mascRNA or tRNAA sequence is in italicized lowercase letters and shaded in grey; the aptamer sequence is wave underlined. The sequences that form the effector region stem are double underlined.

DETAILED DESCRIPTION OF THE INVENTION

Figure 1A:
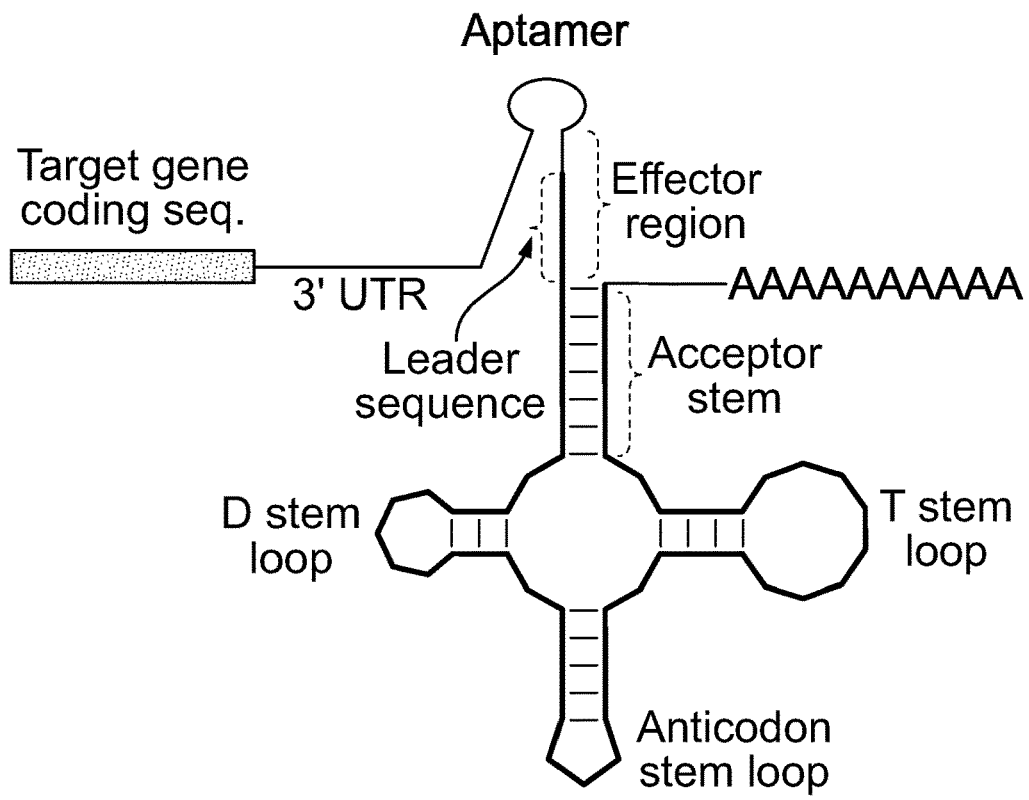
FIG. 1a. A schematic of one embodiment in which the polynucleotide cassette is inserted in the 3' untranslated region (UTR) of a target gene. In this embodiment, the effector sequence of the riboswitch includes sequence complementary to the leader sequence. When no ligand is present the effector sequence does not form a stem that includes the leader sequence. The leader sequence is accessible to RNase P and the RNA is cleaved leading to degradation and preventing (or reducing) expression of the target gene.
Figure 1B:
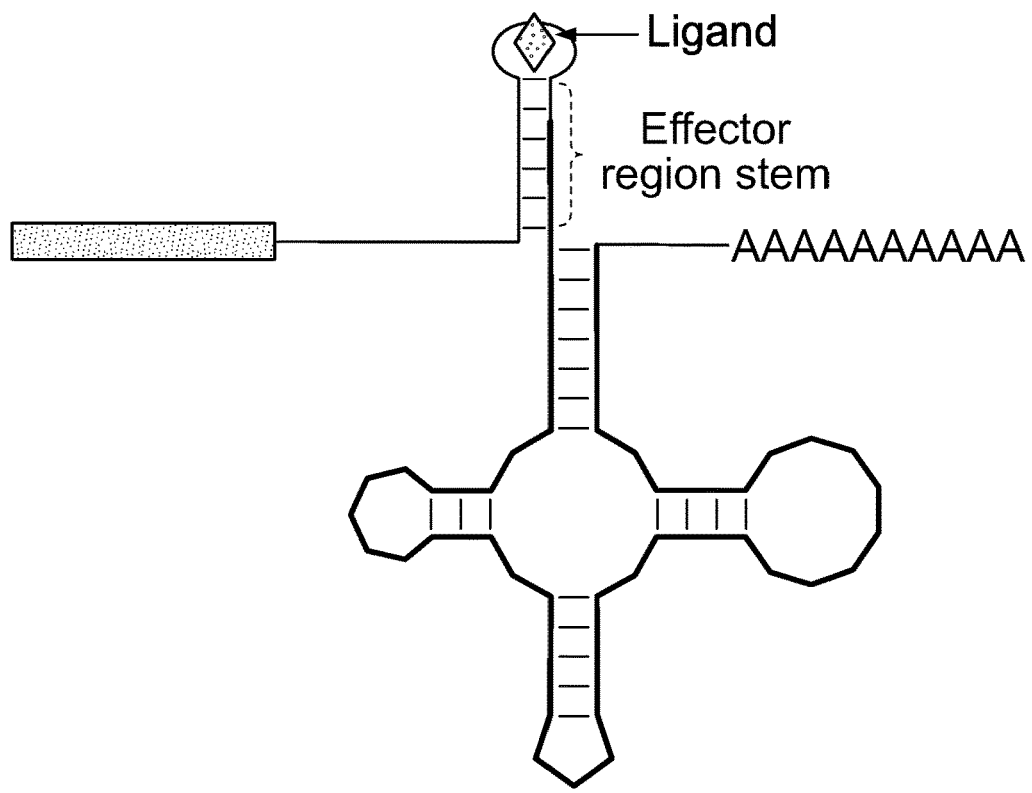
FIG. 1b. A schematic of the polynucleotide cassette from FIG. 1a with a ligand (♦) bound to the aptamer. When the ligand is present, the effector sequence forms a stem that includes the leader sequence of the RNase substrate. The leader sequence is no longer accessible, and the cleavage of the RNA by RNase P is inhibited, leading to increased expression of the target gene.

This application claims priority to U.S. provisional application Ser. No. 62/466,138, filed Mar. 2, 2016, which is incorporated herein in its entirety. The present application refers to a Sequence Listing providing SEQ ID NOs listed below, which is provided herewith as an electronic document and which is incorporated herein by reference in its entirety.

Regulation of the expression of a target gene (e.g., a therapeutic transgene) is useful or necessary in a variety of situations. In the context of the therapeutic expression of genes, techniques that enable regulated expression of transgenes have the potential to enhance safety by regulating the level of expression and its timing. A regulated system to control protein expression has practical and, in some cases, essential roles for safe and effective therapeutic applications. The invention provides polynucleotide cassettes for the modulation of target gene expression by aptamer-mediated ribonuclease cleavage of the RNA of a target gene and methods of using the polynucleotide cassettes to modulate target gene expression in response to the presence or absence of a ligand that binds the aptamer. Endonucleolytic cleavage of mRNA causes, for example, loss of the 5' cap or 3' poly A tail, leading to degradation of the mRNA through the RNA exosome pathway. The present invention thus provides a gene regulation cassette that can be used to regulate the expression of a target gene by providing the aptamer ligand. Such methods are useful, e.g., for the study of target gene expression in cells, tissues, and organisms, or for the regulation of the expression level of a therapeutic protein.

The gene regulation polynucleotide cassette refers to a recombinant DNA construct that, when incorporated into the DNA of a target gene, provides the ability to regulate expression of the target gene by aptamer/ligand mediated ribonuclease cleavage of the resulting RNA. As used herein, a polynucleotide cassette or construct is a nucleic acid (e.g., DNA or RNA) comprising elements derived from different sources (e.g., different organisms, different genes from the same organism, and the like). The polynucleotide cassette comprises a riboswitch and a ribonuclease substrate sequence. The riboswitch in the context of the present invention contains a sensor region (e.g., an aptamer) and an effector region that together are responsible for sensing the presence of a ligand that binds the sensor region and altering cleavage of the ribonuclease substrate sequence by a ribonuclease. In one embodiment, the target gene's expression is increased when the aptamer ligand is present and decreased when the ligand is absent.

Ribonuclease Substrate

The ribonuclease substrate sequence that is linked to the riboswitch can be any ribonuclease substrate that targets a ribonuclease to cleave the target RNA when inserted into the target gene as part of the gene regulation polynucleotide cassette. In one embodiment, the ribonuclease substrate is a RNase P substrate sequence such as a precursor tRNA or a homologous sequence. In other embodiments, the RNase P substrate sequence comprises a sequence encoding mascRNA; MEN beta tRNA-like structure (see Sunwoo et al. Genome Research 2009, 19:347-359; Wilusz et al., Genes Dev. 2012, 26(21):2392-407, both incorporated herein by reference), a viral tRNA-like structure, a RNase P model substrate, and homologous sequences that can initiate RNase P cleavage. Yuan and Altman, in an article published in The EMBO Journal (vol. 14, pp. 159-168, incorporated herein by reference), describe model RNase P substrate sequences including, for example, precursor tyrosine tRNA with the D-loop or anticodon loop deleted (see, e.g., FIGS. 1-4, Table 1, and associated text of Yuan and Altman).

Riboswitch

The term "riboswitch" as used herein refers to a regulatory segment of a RNA polynucleotide, or the DNA sequence encoding the regulatory segment of a RNA polynucleotide. A riboswitch in the context of the present invention contains a sensor region (e.g., an aptamer) and an effector region that together are responsible for sensing the presence of a ligand (e.g., a small molecule) and modulating the suitability of ribonuclease substrate sequence for cleavage by a ribonuclease. In one embodiment, the ribonuclease is RNase P. In one embodiment, the riboswitch is recombinant, utilizing polynucleotides from two or more sources. The term "synthetic" as used herein in the context of a riboswitch refers to a riboswitch that is not naturally occurring. In one embodiment, the sensor and effector regions are joined by a polynucleotide linker. In one embodiment, the polynucleotide linker forms a RNA stem (i.e., a region of the RNA polynucleotide that is double-stranded).

The aptamer portion of the riboswitch may be located at the 5' end, 3' end, and/or within a stem loop of the RNase P substrate. When the aptamer is linked to the 5' end of the RNase P substrate sequence, the effector region of the riboswitch may include sequence that is complementary to all or part of the RNase P substrate leader sequence (see, e.g., FIGS. 1a, 1b and 3b). In this configuration (i.e., the riboswitch at the 5' end of the substrate), the effector region of the riboswitch may also include sequence that is complementary to all or part of the 5' acceptor stem sequence of the RNase P substrate (for example, as in the GM1 and GM2 constructs).

When the aptamer portion of the riboswitch is located at the 3' end of the RNase P substrate (as in the MG1-4 constructs) the effector region comprises sequence that is complementary to all or part of the 3' acceptor stem sequence of the RNase P substrate. In other embodiments, the aptamer portion of the riboswitch is located in a stem-loop of the RNase P substrate sequence. In some embodiments, the aptamer portion of the riboswitch sequence is located in the D stem-loop, T stem loop, anticodon stem loop, or variable loop of the RNase P substrate sequence. When the riboswitch is located in the D stem loop, the effector region may include all or part of the D stem. Likewise, when the aptamer is located in the T stem loop, the anticodon stem loop, or the variable loop the effector region may include all or part of the T stem, the anticodon stem, or the variable loop stem, respectively.

Effector Region

The effector region of the riboswitch comprises RNA sequence that, in response to ligand binding the sensor region (e.g., an aptamer), alters the susceptibility of the ribonuclease substrate to ribonuclease cleavage. In one embodiment, the effector region comprises all or part of the leader sequence of an RNase P substrate sequence. In this embodiment, the effector region stem comprises some or all of the leader sequence and sequence that is complementary to some or all of the leader sequence. When the aptamer binds its ligand, the effector region forms a stem that includes leader sequence thereby preventing cleavage of the target RNA by RNase P (see, e.g., FIG. 1b). Under certain conditions (for example, when the aptamer is not bound to its ligand), the effector region is in a context that provides access to the leader sequence leading to cleavage by RNase P (see, e.g., FIG. 1a and FIG. 3b). In other embodiments, the effector region stem includes, in addition to leader sequence (and its complement), one or more nucleotides of the acceptor stem of the RNase P substrate, and sequence complementary to the one or more nucleotides of the acceptor stem (as in the GM1 and GM2 constructs). In embodiments other embodiments, there are 1 or more nucleotides of the 3' leader sequence of the RNase P substrate that are not part of the effector region stem (see, e.g., constructs GM6, GM7 and GM8). In other words, in these embodiments, sequence forming effector region stem and sequence forming the acceptor stem of the RNase P substrate do not overlap and may be separated by 0, 1, 2, 3, or 4 nucleotides.

Figure 3A:
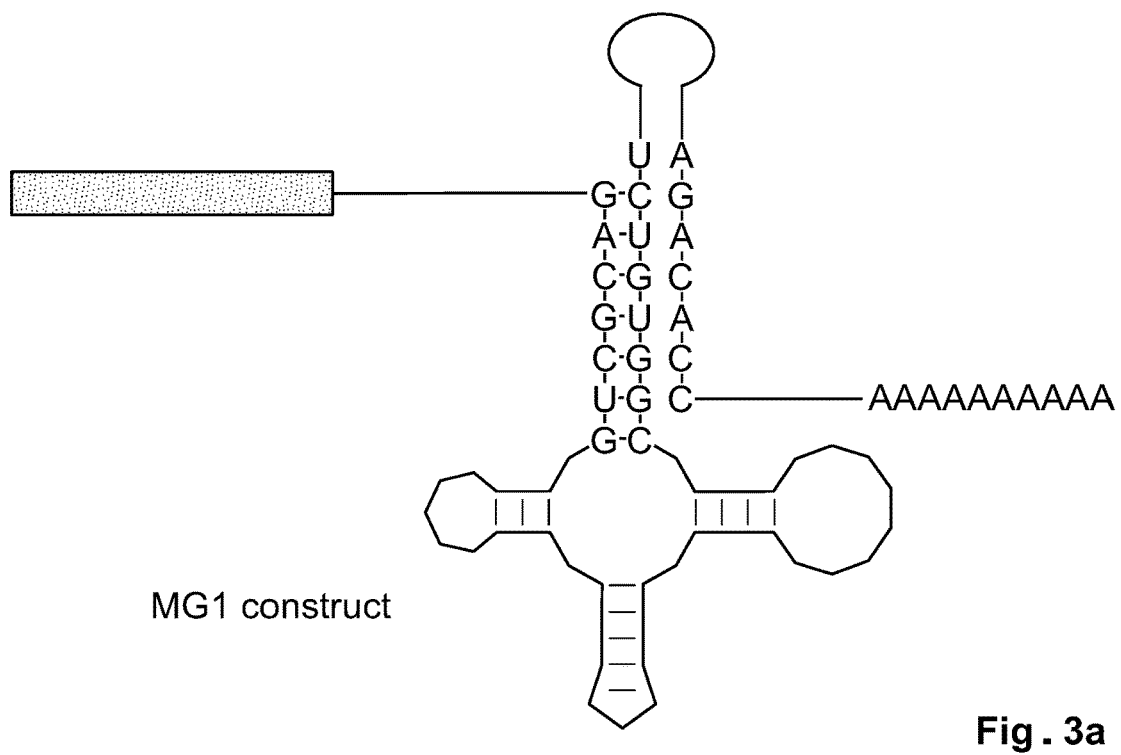
FIG. 3a. Schematic of the mRNA transcript from the MG1 (SEQ ID NO: 1) polynucleotide cassette.

In some embodiments, the effector region comprises some or all of the acceptor stem of the RNase P substrate sequence (see, e.g., FIG. 3a). In this embodiment, the effector region stem comprises some or all of the acceptor stem sequence and sequence that is complementary to some or all of the acceptor stem sequence. When the aptamer binds its ligand, the effector region forms a stem that includes acceptor stem sequence thereby disrupting the acceptor stem structure and preventing cleavage of the target RNA by RNase P. Under certain conditions (for example, when the aptamer is not bound to its ligand), the effector region is in a context that allows the acceptor stem structure leading to cleavage by RNase P. In embodiments of the invention the effector region stem comprises 1, 2, 3, 4, 5, or 6, nucleotides of the acceptor stem of the RNase P substrate and the complementary sequence. In other embodiments, the effector region comprises all or part of the stem of the D stem loop, T stem loop, variable loop, or anticodon stem loop.

The portion of the effector region that is capable of forming a stem upon ligand binding the aptamer should be of a sufficient length (and GC content) to substantially prevent ribonuclease cleavage of the substrate upon ligand binding the aptamer, while also allowing the ribonuclease substrate to be cleaved by the ribonuclease when ligand is not present in sufficient quantities. In embodiments of the invention, the stem portion of the effector region comprises stem sequence in addition to the ribonuclease substrate sequence and its complementary sequence. In some embodiments, this additional stem sequence comprises sequence from the aptamer stem. The length and sequence of the effector region stem can be modified using known techniques in order to identify stems that allow acceptable background expression of the target gene when no ligand is present and acceptable expression levels of the target gene when the ligand is present. If the effector region stem is, for example, too long it may hide access to the leader sequence, or otherwise prevent the substrate from being cleaved by the ribonuclease in the presence or absence of ligand. If the stem is too short, it may not form a stable stem capable of sequestering leader sequence (or otherwise may not alter the substrate conformation) in which case the target RNA will be cleaved in the presence or absence of ligand. In one embodiment, the total length of the effector region stem is between about 7 base pairs to about 20 base pairs. In some embodiments, the length of the stem is between about 8 base pairs to about 11 base pairs. In some embodiments, the length of the stem is 8 base pairs to 11 base pairs. In addition to the length of the stem, the GC base pair content of the stem can be altered to modify the stability of the stem.

Aptamer/Ligand

In one embodiment, the sensor region comprises an aptamer. The term "aptamer" as used herein refers to an RNA polynucleotide that specifically binds to a ligand. The term "ligand" refers to a molecule that is specifically bound by an aptamer. In one embodiment, the ligand is a small molecule, i.e., a low molecular weight (less than about 1,000

Daltons) molecule including, for example, lipids, monosaccharides, second messengers, co-factors, metal ions, other natural products and metabolites, nucleic acids, as well as most therapeutic drugs. In one embodiment, the ligand is a polynucleotide with 2 or more nucleotide bases.

In one embodiment, the ligand is selected from the group consisting of 8-azaguanine, adenosine 5'-monophosphate monohydrate, amphotericin B, avermectin B1, azathioprine, chlormadinone acetate, mercaptopurine, moricizine hydrochloride, N6-methyladenosine, nadide, progesterone, promazine hydrochloride, pyrvinium pamoate, sulfaguanidine, testosterone propionate, thioguanosine, tyloxapol and vorinostat.

Aptamer ligands can also be cell endogenous components that increase significantly under specific physiological/pathological conditions, such as oncogenic transformation—these may include second messenger molecules such as GTP or GDP, calcium; fatty acids, or fatty acids that are incorrectly metabolized such as 13-HODE in breast cancer (Flaherty, J T et al., Plos One, Vol. 8, e63076, 2013, incorporated herein by reference); amino acids or amino acid metabolites; metabolites in the glycolysis pathway that usually have higher levels in cancer cells or in normal cells in metabolic diseases; and cancer-associated molecules such as Ras or mutant Ras protein, mutant EGFR in lung cancer, indoleamine-2,3-dioxygenase (IDO) in many types of cancers. Endogenous ligands include progesterone metabolites in breast cancer as disclosed by J P Wiebe (Endocrine-Related Cancer (2006) 13:717-738, incorporated herein by reference). Endogenous ligands also include metabolites with increased levels resulting from mutations in key metabolic enzymes in kidney cancer such as lactate, glutathione, kynurenine as disclosed by Minton, D R and Nanus, D M (Nature Reviews, Urology, Vol. 12, 2005, incorporated herein by reference).

Aptamers have binding regions that are capable of forming complexes with an intended target molecule (i.e., the ligand). The specificity of the binding can be defined in terms of the comparative dissociation constants (Kd) of the aptamer for its ligand as compared to the dissociation constant of the aptamer for unrelated molecules. Thus, the ligand is a molecule that binds to the aptamer with greater affinity than to unrelated material. Typically, the Kd for the aptamer with respect to its ligand will be at least about 10-fold less than the Kd for the aptamer with unrelated molecules. In other embodiments, the Kd will be at least about 20-fold less, at least about 50-fold less, at least about 100-fold less, and at least about 200-fold less. An aptamer will typically be between about 15 and about 200 nucleotides in length. More commonly, an aptamer will be between about 30 and about 100 nucleotides in length.

The aptamers that can be incorporated as part of the riboswitch can be a naturally occurring aptamer, or modifications thereof, or aptamers that are designed de novo and/or screened through systemic evolution of ligands by exponential enrichment (SELEX) or other screening methods. Examples of aptamers that bind small molecule ligands include, but are not limited to theophylline, dopamine, sulforhodamine B, cellobiose, kanamycin A, lividomycin, tobramycin, neomycin B, viomycin, chloramphenicol, streptomycin, cytokines, cell surface molecules, and metabolites. For a review of aptamers that recognize small molecules, see, e.g., Famulok, Science 9:324-9 (1999) and McKeague, M. & DeRosa, M. C. J. Nuc. Aci. 2012 (both of which are incorporated herein by reference). In another embodiment, the aptamer is a complementary polynucleotide.

Methods for Identifying Aptamer/Ligand

In one embodiment, the aptamer is designed to bind a particular small molecule ligand. Methods for designing and selecting aptamers that bind particular ligands are disclosed in WO/2018/025085, incorporated herein by reference. Other methods for screening aptamers include, for example, SELEX. Methods for designing aptamers that selectively bind a small molecule using SELEX are disclosed in, e.g., U.S. Pat. Nos. 5,475,096, 5,270,163, and Abdullah Ozer, et al. Nuc. Aci. 2014, which are incorporated herein by reference. Modifications of the SELEX process are described in U.S. Pat. Nos. 5,580,737 and 5,567,588, which are incorporated herein by reference.

Selection techniques for identifying aptamers generally involve preparing a large pool of DNA or RNA molecules of the desired length that contain a region that is randomized or mutagenized. For example, an oligonucleotide pool for aptamer selection might contain a region of 20-100 randomized nucleotides flanked by regions of defined sequence that are about 15-25 nucleotides long and useful for the binding of PCR primers. The oligonucleotide pool is amplified using standard PCR techniques, or other means that allow amplification of selected nucleic acid sequences. The DNA pool may be transcribed in vitro to produce a pool of RNA transcripts when an RNA aptamer is desired. The pool of RNA or DNA oligonucleotides is then subjected to a selection based on their ability to bind specifically to the desired ligand. Selection techniques include, for example, affinity chromatography, although any protocol which will allow selection of nucleic acids based on their ability to bind specifically to another molecule may be used. Selection techniques for identifying aptamers that bind small molecules and function within a cell may involve cell based screening methods. In the case of affinity chromatography, the oligonucleotides are contacted with the target ligand that has been immobilized on a substrate in a column or on magnetic beads. The oligonucleotide is preferably selected for ligand binding in the presence of salt concentrations, temperatures, and other conditions which mimic normal physiological conditions. Oligonucleotides in the pool that bind to the ligand are retained on the column or bead, and nonbinding sequences are washed away. The oligonucleotides that bind the ligand are then amplified (after reverse transcription if RNA transcripts were utilized) by PCR (usually after elution). The selection process is repeated on the selected sequences for a total of about three to ten iterative rounds of the selection procedure. The resulting oligonucleotides are then amplified, cloned, and sequenced using standard procedures to identify the sequences of the oligonucleotides that are capable of binding the target ligand. Once an aptamer sequence has been identified, the aptamer may be further optimized by performing additional rounds of selection starting from a pool of oligonucleotides comprising a mutagenized aptamer sequence.

In vivo aptamer screening may be used following one or more rounds of in vitro selection (e.g., SELEX). For example, Konig, J. et al. (RNA. 2007, 13(4):614-622, incorporated herein by reference) describe combining SELEX and a yeast three-hybrid system for in vivo selection of aptamer.

Target Genes

The gene regulation cassette of the present invention is a platform that can be used to regulate the expression of any target gene that can be expressed in a target cell, tissue or organism. The term "target gene" refers to a polynucleotide that is introduced into a cell and is capable of being transcribed into RNA and translated and/or expressed under appropriate conditions. Alternatively, the target gene is endogenous to the target cell and the gene regulation cassette of the present invention is positioned into the target gene (for example into the 5' or 3' UTR of an endogenous target gene). An example of a target gene is a polynucleotide encoding a therapeutic polypeptide. In another embodiment, the target gene encodes an RNA such as a miRNA, rRNA, small or long noncoding RNAs, short hairpin RNA (shRNA) and any other regulatory RNAs. In one embodiment, the target gene is exogenous to the cell in which the recombinant DNA construct is to be transcribed. In another embodiment, the target gene is endogenous to the cell in which the recombinant DNA construct is to be transcribed.

The target gene according to the present invention may be a gene encoding a protein, or a sequence encoding a non-protein coding RNA. The target gene may be, for example, a gene encoding a structural protein, an enzyme, a cell signaling protein, a mitochondrial protein, a zinc finger protein, a hormone, a transport protein, a growth factor, a cytokine, an intracellular protein, an extracellular protein, a transmembrane protein, a cytoplasmic protein, a nuclear protein, a receptor molecule, an RNA binding protein, a DNA binding protein, a transcription factor, translational machinery, a channel protein, a motor protein, a cell adhesion molecule, a mitochondrial protein, a metabolic enzyme, a kinase, a phosphatase, exchange factors, a chaperone protein, and modulators of any of these. In embodiments, the target gene encodes erythropoietin (Epo), human growth hormone (hGH), transcription activator-like effector nucleases (TALEN), human insulin, CRISPR associated protein 9 (cas9), or an immunoglobulin (or portion thereof), including, e.g., a therapeutic antibody.

Expression Constructs

The present invention contemplates the use of a recombinant vector for introduction into target cells a polynucleotide encoding a target gene and containing the gene regulation cassette described herein. In many embodiments, the recombinant DNA construct of this invention includes additional DNA elements including DNA segments that provide for the replication of the DNA in a host cell and expression of the target gene in that cell at appropriate levels. The ordinarily skilled artisan appreciates that expression control sequences (promoters, enhancers, and the like) are selected based on their ability to promote expression of the target gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors.

Viral vectors for the aptamer-mediated expression of a target gene in a target cell, tissue, or organism are known in the art and include adenoviral (AV) vectors, adeno-associated virus (AAV) vectors, retroviral and lentiviral vectors, and Herpes simplex type 1 (HSV1) vectors.

Adenoviral vectors include, for example, those based on human adenovirus type 2 and human adenovirus type 5 that have been made replication defective through deletions in the E1 and E3 regions. The transcriptional cassette can be inserted into the E1 region, yielding a recombinant E1/E3-deleted AV vector. Adenoviral vectors also include helper-dependent high-capacity adenoviral vectors (also known as high-capacity, "gutless" or "gutted" vectors), which do not contain viral coding sequences. These vectors, contain the cis-acting elements needed for viral DNA replication and packaging, mainly the inverted terminal repeat sequences (ITR) and the packaging signal ($\Psi$). These helper-dependent AV vector genomes have the potential to carry from a few hundred base pairs up to approximately 36 kb of foreign DNA.

Recombinant adeno-associated virus "rAAV" vectors include any vector derived from any adeno-associated virus serotype, including, without limitation, AAV-1, AAV-2, AAV-3, AAV-4, AAV-5, AAV-7 and AAV-8, AAV-9, AAV-10, and the like. rAAV vectors can have one or more of the AAV wild-type genes deleted in whole or in part, preferably the Rep and/or Cap genes, but retain functional flanking ITR sequences. Functional ITR sequences are retained for the rescue, replication, packaging and potential chromosomal integration of the AAV genome. The ITRs need not be the wild-type nucleotide sequences, and may be altered (e.g., by the insertion, deletion or substitution of nucleotides) so long as the sequences provide for functional rescue, replication and packaging.

Alternatively, other systems such as lentiviral vectors can be used in embodiments of the invention. Lentiviral-based systems can transduce non-dividing as well as dividing cells making them useful for applications targeting, for examples, the non-dividing cells of the CNS. Lentiviral vectors are derived from the human immunodeficiency virus and, like that virus, integrate into the host genome providing the potential for long-term gene expression.

Polynucleotides, including plasmids, YACs, minichromosomes and minicircles, carrying the target gene containing the gene regulation cassette can also be introduced into a cell or organism by nonviral vector systems using, for example, cationic lipids, polymers, or both as carriers. Conjugated poly-L-lysine (PLL) polymer and polyethylenimine (PEI) polymer systems can also be used to deliver the vector to cells. Other methods for delivering the vector to cells includes hydrodynamic injection and electroporation and use of ultrasound, both for cell culture and for organisms. For a review of viral and non-viral delivery systems for gene delivery see Nayerossadat, N. et al. (Adv Biomed Res. 2012; 1:27) incorporated herein by reference.

Methods of Modulating Expression of a Target Gene

In one aspect, this invention provides a method of modulating expression of a target gene (e.g., a therapeutic gene), by (a) inserting the gene regulation cassette of the present invention into a target gene; (b) introducing the target gene comprising the gene regulation cassette into a cell; and (c) exposing the cell to a ligand that binds the aptamer. In one embodiment, the ligand is a small molecule. In aspects, expression of the target gene in target cells confers a desired property to a cell into which it was introduced, or otherwise leads to a desired therapeutic outcome. The target cells are Eukaryotic cells, for example mammalian cells. In embodiments, target cells are human cells from a target tissue, including, for example, adipose, central nervous system (CNS), muscle, cardiac, ocular, hepatic, and the like.

In a preferred embodiment, one or more gene regulation cassettes are inserted into the 5' and/or 3' untranslated region of the target gene. In one embodiment, a single gene regulation cassette is inserted into the target gene. In other embodiments 2, 3, 4, or more gene regulation cassettes are inserted in the target gene. In one embodiment, two gene regulation cassettes are inserted into the target gene. When multiple gene regulation cassettes are inserted into a target gene, they each can contain the same aptamer such that a single ligand can be used to modulate ribonuclease cleavage of the multiple cassettes and thereby modulate target gene expression. In other embodiments, multiple gene regulation cassettes are inserted into a target gene, each can contain a different aptamer so that exposure to multiple different small molecule ligands modulates target gene expression. In other embodiments, multiple gene regulation cassettes are inserted into a target gene, each containing different ribonuclease substrate sequences. This may be useful in reducing recombination and improving ease of incorporation into viral vectors.

The polynucleotide cassette of the present invention can be used in combination with other mechanisms for the regulation of expression of the target gene. In one embodiment, a polynucleotide cassette of the present invention is used in combination with a gene regulation cassette that modulates target gene expression by aptamer-mediated regulation of alternative splicing as described in WO 2016/126747, incorporated herein by reference. The present invention can also be combined with the polynucleotide constructs and methods described in PCT/US2017/016303 and PCT/US1207/016279, incorporated herein by reference.

Methods of Treatment and Pharmaceutical Compositions

One aspect of the invention provides a method of regulating the level of a therapeutic protein delivered by gene therapy. In this embodiment, the "target gene" may encode the therapeutic protein. The "target gene" may encode a protein that is endogenous or exogenous to the cell.

The therapeutic gene sequence containing the regulatory cassette with aptamer-driven riboswitch is delivered to target cells in vitro or ex vivo, e.g., by a vector. The cell specificity of the "target gene" may be controlled by promoter or other elements within the vector. Delivery of the vector construct containing the target gene and the polynucleotide cassette, and the transfection of the target tissues resulting in stable transfection of the regulated target gene, is the first step in producing the therapeutic protein.

However, due to the presence of the regulatory cassette within the target gene sequence, the target gene is not expressed at significant levels, i.e., it is in the "off state" in the absence of the specific ligand that binds to the aptamer contained within in the regulatory cassette riboswitch. Only when the aptamer specific ligand is administered (or otherwise present in sufficient quantities) is the target gene expression activated.

The delivery of the vector construct containing the target gene and the delivery of the activating ligand generally are separated in time. The delivery of the activating ligand will control when the target gene is expressed, as well as the level of protein expression. The ligand may be delivered by a number of routes including, but not limited to, oral, intramuscular (IM), intravenous (IV), intraocular, or topically.

The timing of delivery of the ligand will depend on the requirement for activation of the target gene. For example, if the therapeutic protein encoded by the target gene is required constantly, an oral small molecule ligand may be delivered daily, or multiple times a day, to ensure continual activation of the target gene, and thus continual expression of the therapeutic protein. If the target gene has a long acting effect, the inducing ligand may be dosed less frequently.

This invention allows the expression of the therapeutic transgene to be controlled temporally, in a manner determined by the temporal dosing of the ligand specific to the aptamer within the riboswitch of the regulatory polynucleotide cassette. The increased expression of the therapeutic transgene only on ligand administration, increases the safety of a gene therapy treatment by allowing the target gene to be off in the absence of the ligand.

Different aptamers can be used to allow different ligands to activate target genes. In certain embodiments of the invention, each therapeutic gene containing a regulatory cassette will have a specific aptamer within the cassette that will be activated by a specific small molecule. This means that each therapeutic gene can be activated only by the ligand specific to the aptamer housed within it. In these embodiments, each ligand will only activate one therapeutic gene. This allows for the possibility that several different "target genes" may be delivered to one individual and each will be activated on delivery of the specific ligand for the aptamer contained within the regulatory cassette housed in each target gene.

This invention allows any therapeutic protein whose gene can be delivered to the body (such as erythropoietin (EPO) or a therapeutic antibody) to be produced by the body when the activating ligand is delivered. This method of therapeutic protein delivery may replace the manufacture of such therapeutic proteins outside of the body which are then injected or infused, e.g., antibodies used in cancer or to block inflammatory or autoimmune disease. The body containing the regulated target gene becomes the biologics manufacturing factory, which is switched on when the gene-specific ligand is administered.

Dosing levels and timing of dosing of a therapeutic protein may be important to therapeutic effect. For example, in the delivery of AVASTIN (anti-VEGF antibody) for cancer. The present invention increases the ease of dosing in response to monitoring for therapeutic protein levels and effects.

In one embodiment, the target gene may encode a nuclease that can target and edit a particular DNA sequence. Such nucleases include Cas9, zinc finger containing nucleases, or TALENs. In the case of these nucleases, the nuclease protein may be required for only a short period of time that is sufficient to edit its target endogenous gene. However, if an unregulated nuclease gene is delivered to the body, this protein may be present for the rest of the life of the cell. In the case of nucleases, there is an increasing risk of off-target editing the longer the nuclease is present. Regulation of expression of such proteins has a significant safety advantage. In this case, a vector containing the nuclease gene containing the regulatory cassette can be delivered to the appropriate cells in the body. The nuclease gene is in the "off" state in the absence of the cassette-specific ligand, so no nuclease is produced. Only when the activating ligand is administered, is the nuclease produced. When sufficient time has elapsed allowing sufficient editing to occur, the ligand is withdrawn and not administered again. Thus, the nuclease gene is thereafter in the "off" state and no further nuclease is produced and editing stops. This approach may be used to correct genetic conditions, including a number of inherited retinopathies such as LCA10 caused by mutations in CEP290 and Stargardts disease caused by mutations in ABCA4.

Administration of a regulated target gene encoding a therapeutic protein which is activated only on specific ligand administration may be used to regulate therapeutic genes to treat many different types of diseases, e.g., cancer with therapeutic antibodies, immune disorders with immune modulatory proteins or antibodies, metabolic diseases, rare diseases such as PNH with anti-C5 antibodies or antibody fragments as the regulated gene, or ocular angiogenesis with therapeutic antibodies, and dry AMD with immune modulatory proteins.

A wide variety of specific target genes, allowing for the treatment of a wide variety of specific diseases and conditions, are suitable for use in the present invention. For example, insulin or an insulin analog (preferably human insulin or an analog of human insulin) may be used as the target gene to treat type I diabetes, type II diabetes, or metabolic syndrome; human growth hormone may be used as the target gene to treat children with growth disorders or growth hormone-deficient adults; erythropoietin (preferably human erythropoietin) may be used as the target gene to treat anemia due to chronic kidney disease, anemia due to myelodysplasia, or anemia due to cancer chemotherapy.

The present invention may be especially suitable for treating diseases caused by single gene defects such as cystic fibrosis, hemophilia, muscular dystrophy, thalassemia, or sickle cell anemia. Thus, human $\beta$-, $\gamma$-, $\delta$-, or $\zeta$-globin may be used as the target gene to treat $\beta$-thalassemia or sickle cell anemia; human Factor VIII or Factor IX may be used as the target gene to treat hemophilia A or hemophilia B.

The ligands used in the present invention are generally combined with one or more pharmaceutically acceptable carriers to form pharmaceutical compositions suitable for administration to a patient. Pharmaceutically acceptable carriers include solvents, binders, diluents, disintegrants, lubricants, dispersion media, coatings, antibacterial and antifungal agents, isotonic and absorption delaying agents, and the like, generally used in the pharmaceutical arts. Pharmaceutical compositions may be in the form of tablets, pills, capsules, troches, and the like, and are formulated to be compatible with their intended route of administration. Examples of routes of administration include parenteral, e.g., intravenous, intradermal, intranasal, subcutaneous, oral, inhalation, transdermal (topical), transmucosal, and rectal.

The pharmaceutical compositions comprising ligands are administered to a patient in a dosing schedule such that an amount of ligand sufficient to desirably regulate the target gene is delivered to the patient. When the ligand is a small molecule and the dosage form is a tablet, capsule, or the like, preferably the pharmaceutical composition comprises from 0.1 mg to 10 g of ligand; from 0.5 mg to 5 g of ligand; from 1 mg to 1 g of ligand; from 2 mg to 750 mg of ligand; from 5 mg to 500 mg of ligand; or from 10 mg to 250 mg of ligand.

The pharmaceutical compositions may be dosed once per day or multiple times per day (e.g., 2, 3, 4, 5, or more times per day). Alternatively, pharmaceutical compositions may be dosed less often than once per day, e.g., once every 2, 3, 4, 5, 6, 7, 8, 9, 10, 11, 12, 13, or 14 days, or once a month or once every few months. In some embodiments of the invention, the pharmaceutical compositions may be administered to a patient only a small number of times, e.g., once, twice, three times, etc.

The present invention provides a method of treating a patient in need of increased expression of a therapeutic protein encoded by a target gene, the method comprising administering to the patient a pharmaceutical composition comprising a ligand for an aptamer, where the patient previously had been administered a recombinant DNA comprising the target gene, where the target gene contains a gene regulation cassette of the present invention where the riboswitch (containing the aptamer) modulates RNase P cleavage of a RNase P substrate in response to the aptamer ligand.

Articles of Manufacture and Kits

Also provided are kits or articles of manufacture for use in the methods described herein. In aspects, the kits comprise the compositions described herein (e.g., for compositions for delivery of a vector comprising the target gene containing the gene regulation cassette) in suitable packaging. Suitable packaging for compositions (such as ocular compositions for injection) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing the administration, including e.g., any methods described herein. For example, in some embodiments, the kit comprises rAAV for expression of the target gene comprising the gene regulation cassette of the present invention, a pharmaceutically acceptable carrier suitable for injection, and one or more of: a buffer, a diluent, a filter, a needle, a syringe, and a package insert with instructions for performing the injections. In some embodiments, the kit is suitable for intraocular injection, intramuscular injection, intravenous injection and the like.

"Homology" and "homologous" as used herein refer to the percent of identity between two polynucleotide sequences or between two polypeptide sequences. The correspondence between one sequence to another can be determined by techniques known in the art. For example, homology can be determined by a direct comparison of two polypeptide molecules by aligning the sequence information and using readily available computer programs. Two polynucleotide or two polypeptide sequences are "substantially homologous" to each other when, after optimally aligned with appropriate insertions or deletions, at least about 80%, at least about 85%, at least about 90%, and at least about 95% of the nucleotides or amino acids, respectively, match over a defined length of the molecules, as determined using the methods above.

"Percent sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity. Alignment for purposes of determining percent amino acid or nucleic acid sequence identity can be achieved in ways known to the ordinarily-skilled artisan, for example, using publicly available computer software programs including BLAST, BLAST-2, ALIGN or Megalign (DNASTAR) software.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

"Heterologous" or "exogenous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLES

Example 1

Insertion of a tRNA-Like Structure (mascRNA) in the 3' UTR or 5' UTR Causes Cleavage of mRNA and Reduced Protein Expression Experimental Procedure:

Plasmid constructs: DNA fragments containing mouse mascRNA sequence and restriction sites at each end were synthesized (IDT), and digested and cloned into a plasmid backbone Con 8 that contains CMV enhancer/promoter and human beta-globin polyadenylation sequence. All constructs were verified by DNA sequencing (Genewiz).

Northern blot analysis: Locked Nucleic Acid (LNA)-modified oligonucleotides containing sequence tggaaaccaggagtgcca (SEQ ID NO:19) that detects both human and mouse mascRNA, was designed and synthesized by Exiqon, and labeled with Digoxigenin using the DIG Oligonucleotide Tailing Kit (Roche). Non-radioactive Northern blot was performed following the published protocol (Kim, S. W. et al. A sensitive non-radioactive northern blot method to detect small RNAs. Nucleic Acids Res. 38, e98 (2010)).

Flow cytometry analysis: $1.5 \times 10^5$ HeLa cells were plated in 24-well plate the day before transfection. Cells were transfected with 0.2 µg of plasmid DNA using Lipofectamine 2000 following the manufacturer's instruction. Forty-eight hours after transfection, the cells were trypsinized and the cell suspension was subjected to flow cytometric analysis for the intensity of GFP fluorescence using a Guava EasyCyte 8HT machine. The resulting data was analyzed using GuavaSoft2.2.2.

Firefly luciferase assay of cultured cells: $3.5 \times 10^4$ HEK 293 cells were plated in 96-well flat bottom plate the day before transfection. Plasmid DNA (500 ng) was added to a tube or a 96-well U-bottom plate. Separately, TransIT-293 reagent (Minis; 1.4 µL) was added to 50 µL opti-mem I media (Life Technologies) and allowed to sit for 5 minutes at room temperature ("RT"). Then, 50 µL of this diluted transfection reagent was added to the DNA, mixed, and incubated at RT for 20 min. Finally, 7 µL of this solution was added to a well of cells in a 96-well plate. 4 hours after transfection, medium containing transfection solution was replaced with fresh medium. 24 hours after media change, plates were removed from the incubator, and equilibrated to RT for several minutes on a lab bench, then aspirated. Glo-lysis buffer (Promega, 100 µL, RT) was added, and the plates allowed to remain at RT for at least 5 minutes. Then, the well contents were mixed by 50 µL trituration, and 20 µL of each sample was mixed with 20 µL of bright-glo reagent (Promega) that had been diluted to 10% in glo-lysis buffer. 96 wells were spaced on an opaque white 384-well plate. Following a 5-min incubation at RT, luminescence was measured using a Tecan machine with 500 mSec read time. The luciferase activity was expressed as mean arbitrary light unit (ALU)±S.D.

Results:

RNase P recognizes precursor tRNA (pre-tRNA) or tRNA-like molecules with tertiary structure and catalyzes hydrolysis reaction to cleave off the leader sequences in pre-tRNA (Kirsebom, L. A. RNase P RNA mediated cleavage: substrate recognition and catalysis. Biochimie 89, 1183-1194 (2007)). To test whether insertion of an RNase P substrate in an mRNA causes mRNA cleavage and reduction in protein expression, mouse mascRNA sequence was introduced into the 3' UTR of GFP reporter gene. The mascRNA (MALAT1-associated small cytoplasmic RNA) is a tRNA-like structure, and produced from long non-coding RNA MALAT1 by RNase P cleavage to form the 5' end and subsequent cleavage by RNase Z to form 3' end of mascRNA (Wilusz, J. E., et al., 3' end processing of a long nuclear-retained noncoding RNA yields a tRNA-like cytoplasmic RNA. Cell 135, 919-932 (2008)). This tRNA-like structure itself, together with a 12-nt non-related leader sequence, is sufficient to recruit RNase P for mascRNA generation.

Figure 2A:
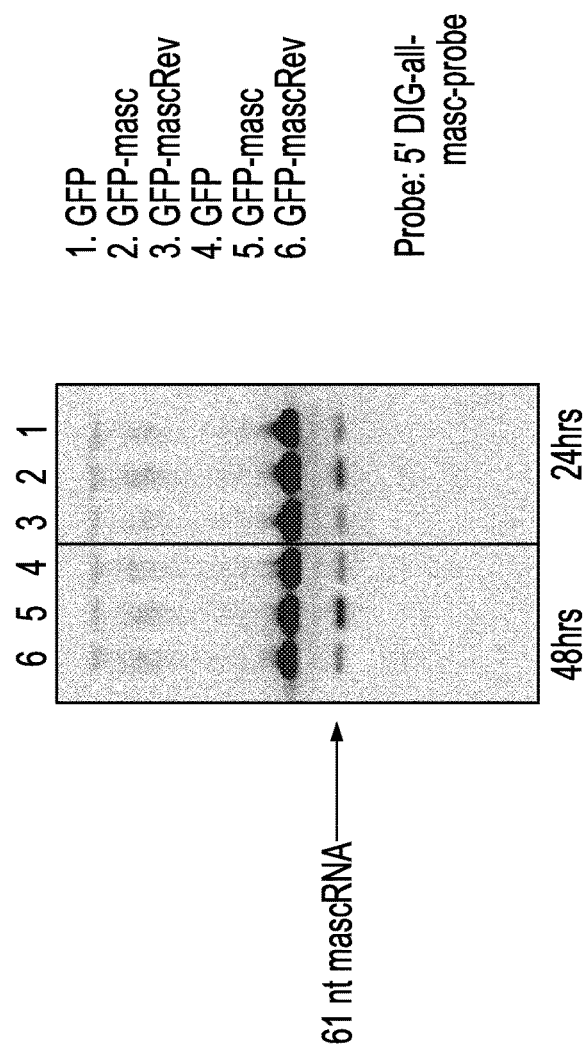
FIG. 2a. Northern blot analysis of the mascRNA. Sequence encoding mascRNA was inserted in the 3' UTR of the target gene (GFP) leading to cleavage of the mRNA and reduced protein expression. HeLa cells transfected with the indicated constructs were collected 24 hours or 48 hours after transfection for RNA extraction. The DIG-labeled probe recognizes both human and mouse mascRNA. Lane 1 and 4 show the endogenous human mascRNA, and lanes 2 and 5 show increased mascRNA expression generated by the mouse mascRNA inserted in the 3' UTR of the GFP reporter gene.

The cleavage of GFP with mascRNA in the 3' UTR was monitored by Northern blot using a probe that can detect both human and mouse mascRNA. The 61nt mascRNA generated from cells that were transfected with GFP-mascRNA (sense) was identified by Norther blot. The 61nt mascRNA was not detected in cells transfected with GFP-mascRNA (antisense) that has mascRNA sequence in reverse orientation (FIG. 2a).

Figure 2B:
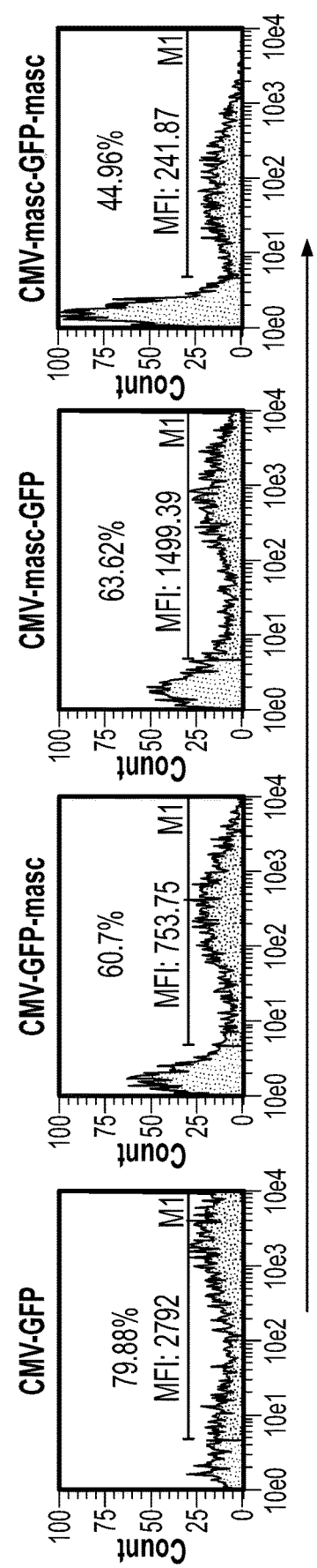
FIG. 2b. Insertion of mascRNA in either the 5' UTR or 3' UTR decreases GFP expression. HeLa cells were transfected with the indicated constructs and were subjected to flow cytometry analysis 48 hours after transfection. The percentage (%) of GFP positive population, as well as the mean fluorescence intensity (MFI), are indicated in the graph. Cells transfected with constructs with mascRNA at 3' UTR (GFP-masc), 5' UTR (masc-GFP), or at both 5' and 3' UTRs (masc-GFP-masc) had decreases in both the percentage of GFP positive cells and MFI, compared to the cells with the control CMV-GFP construct.

At the protein level, cells transfected with GFP-mascRNA construct showed not only a lower percentage of GFP positive population, also decreased mean fluorescence intensity (MFI) in GFP expression, compared to cells with GFP control construct (FIG. 2b, first and second graphs). mascRNA was also inserted in the 5' UTR, as well as in both 5' UTR and 3' UTR, of the GFP reporter gene construct. GFP expression was decreased in cells transfected with mascRNA inserted in the 5' UTR of GFP compared to cells transfected with the GFP control construct (FIG. 2b, 3rd graph). When mascRNA was inserted in both 5' UTR and 3' UTR regions of the GFP reporter construct, GFP expression was further reduced (FIG. 2b, 4th graph).

Figure 2C:
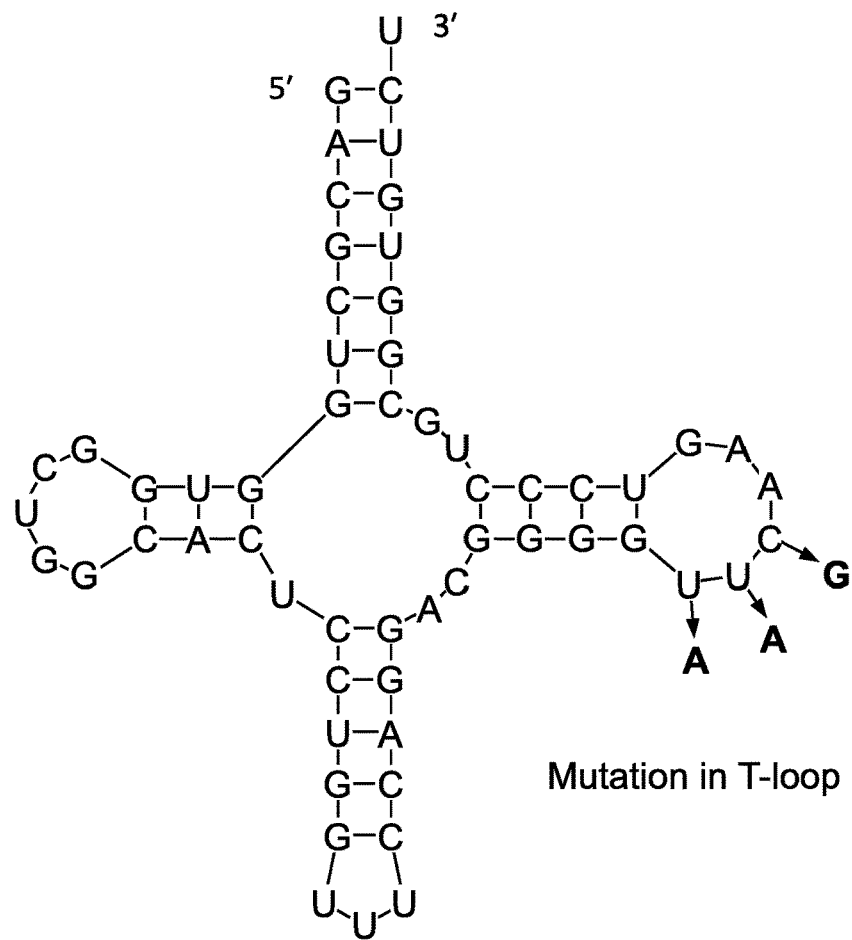
FIG. 2c. Insertion of mascRNA in the 3' UTR decreases luciferase target gene expression. Mouse mascRNA or mutant mouse mascRNA (referred to herein as masc-mlp) was inserted in the 3' UTR of a luciferase gene. The predicted tRNA-like secondary structure of the mouse mascRNA is shown on the upper panel, with the mutation in the T-loop from UUC to AAG indicated. The lower panel shows the result of a luciferase assay. Insertion of mascRNA in the 3' UTR resulted in an 81% decrease in luciferase expression (Luci-masc), whereas cells with a construct containing mutations in the T-loop of the mascRNA (Lucimasc-mlp) only showed 20% reduction in luciferase expression.
Figure 2C:
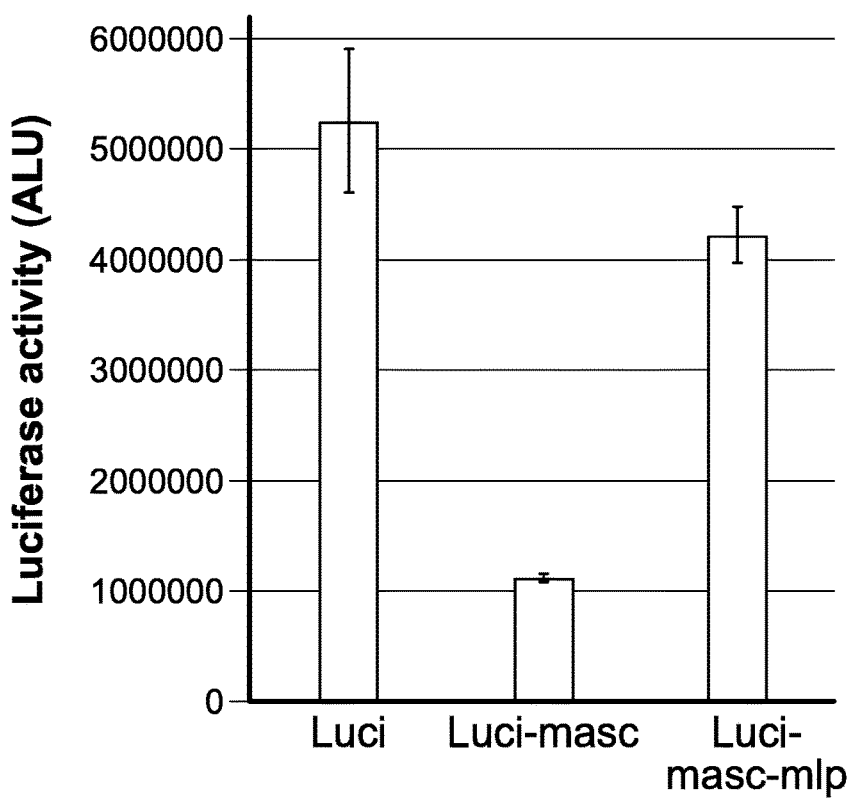

The mascRNA sequence was also inserted into the 3' UTR of a firefly luciferase construct. A negative control (Luci-masc-mlp) was generated by mutating three nucleotides in the T-loop of mascRNA (from UUC to AAG) (see FIG. 2c, left panel). Those three nucleotides are highly conserved in the T-loop of tRNA structures and are required for efficient cleavage by RNase P (Yuan, Y. & Altman, S. Substrate recognition by human RNase P: identification of small, model substrates for the enzyme. EMBO J. 14, 159-168 (1995), incorporated herein by reference). As shown in FIG. 2c (right panel), insertion of mascRNA sequence in 3' UTR region (Luci-masc) decreased the expression of luciferase by 81% comparing to the luciferase construct that has no mascRNA (Luci), indicating that insertion of mascRNA in the 3' UTR caused cleavage of the mRNA and reduced protein expression. However, cells with the luciferase construct that has the mascRNA containing the three mutations in the T-loop (Luci-mascRNA-mlp) showed only 20% reduction in luciferase expression compared to the Luci control, indicating that mutations in the T-loop of mascRNA impairs RNase P-mediated cleavage.

These results demonstrate that insertion of the tRNA-like structure, mascRNA, in either the 3' UTR or 5' UTR leads to RNase P-mediated cleavage of target mRNA and subsequent reduction in protein expression.

Example 2

Use of xpt-Guanine Aptamer to Regulate Target Gene Expression Through Modulating mascRNA-RNase P-Mediated Cleavage of mRNA Experimental Procedures:

Plasmid constructs: oligonucleotide fragments containing mascRNA and guanine aptamer sequences (Mandal, M, et al., Cell 113, 577-586 (2003), incorporated herein by reference) were synthesized (IDT) and cloned into a luciferase (Luci) expression construct (Con8) in the 3' UTR region using compatible restriction sites BamHI and XhoI. All the constructs were verified by DNA sequencing (Genewiz).

Firefly luciferase assay of cultured cells: cells were transfected as described in Example 1. Four hours after transfection, medium containing transfection solution was replaced by medium with either 0.5% DMSO as solvent control or 500 µM guanosine (Sigma) as aptamer ligand. Twenty-two to twenty-four hours after treatment, a luciferase assay was performed as described in Example 1.

Results:

In order to regulate RNase P-mediated cleavage of mRNA, and thereby regulate target gene expression, aptamer sequence linked to mascRNA sequence was inserted in the 3' UTR of a luciferase expression construct, based upon the assumption that in the absence of aptamer ligand, the RNase P cleavage is not affected, therefore, mRNA is cleaved and protein will not be expressed. Upon availability of aptamer ligand, aptamer/ligand binding triggers conformational change of RNA structure, which in turn impairs RNase P cleavage, therefore leaves mRNA intact.

In construct MG1 (SEQ ID NO: 1) (FIG. 3a), a guanine aptamer was inserted immediately downstream the mascRNA sequence, in which a 7-nucleotide sequence following immediately the guanine aptamer sequence is complementary to the last 7 nucleotides of mascRNA. It was rationalized that in this configuration, upon aptamer/ligand binding, the last 7 nucleotides in mascRNA and its complementary sequence would be brought together to form the effector region stem of the riboswitch. Therefore, this 7-nucleotide sequence in mascRNA that is required for tRNA-like structure formation would be embedded in the newly formed aptamer/ligand structure, thus RNase P binding and cleavage would be impaired. Indeed, as shown in FIG. 3c, in the absence of guanosine, insertion of an xpt-G aptamer downstream of mascRNA (MG1) resulted in luciferase activity that was about 68% of that from Luci control construct (a 32% reduction in luciferase activity compared to the Luci control construct). However, in the presence of guanosine, luciferase activity was restored to 100% of the Luci control construct, generating a 2.1-fold induction of luciferase gene expression when comparing guanosine-treated versus solvent control-treated cells. The high level of luciferase activity in the absence of aptamer ligand indicates the low efficiency of RNase P-mediated cleavage.

Figure 3B:
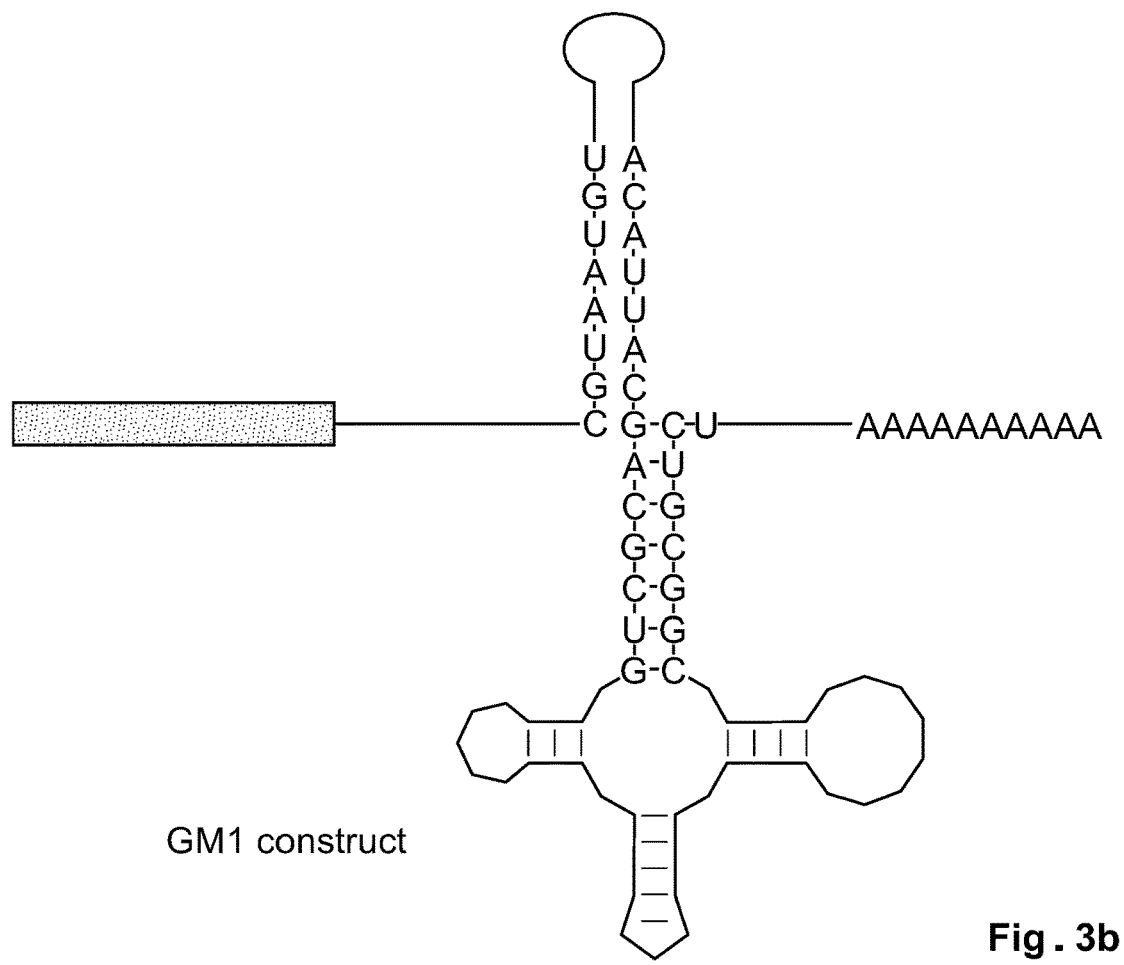
FIG. 3b. Schematic of the mRNA transcript from the GM1 (SEQ ID NO: 2) polynucleotide cassette.
Figure 3C:
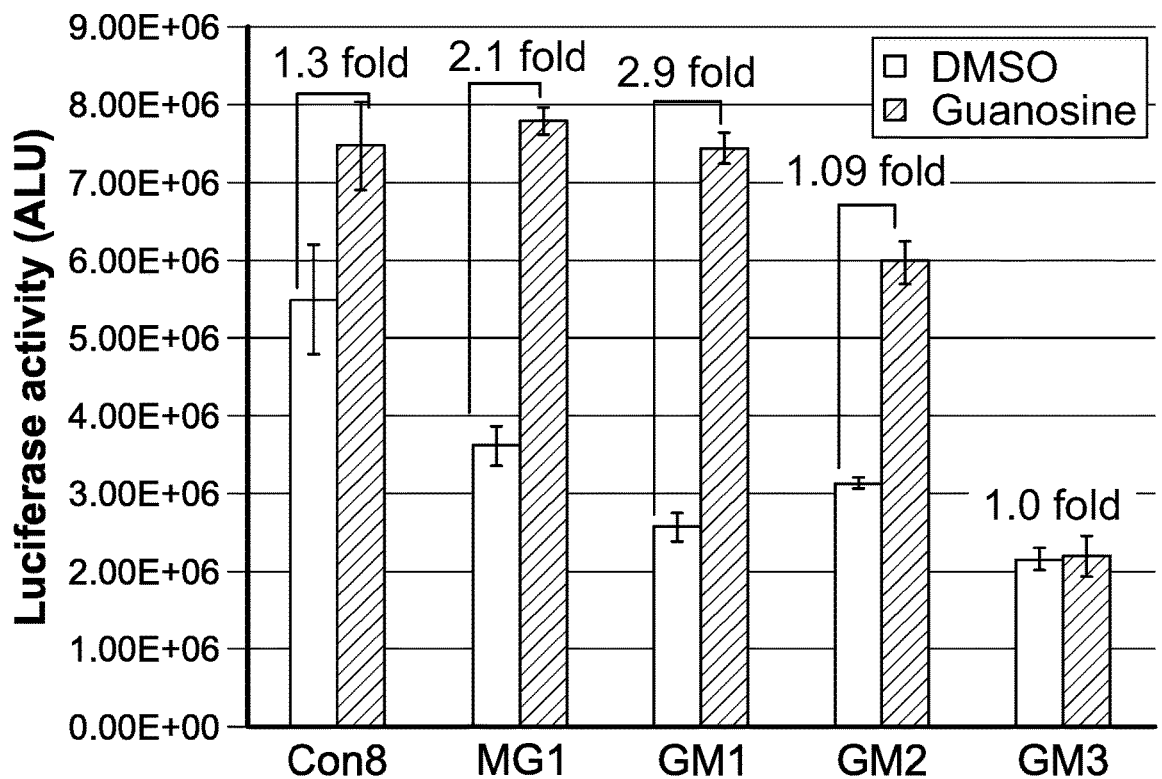
FIG. 3c. Regulating gene expression through aptamer-mediated modulation of RNase P cleavage of mRNA. The results of a luciferase assay are shown. HEK 293 cells were transfected with the indicated luciferase control construct, Con8, or constructs containing both mascRNA and guanine aptamer sequences (MG1, GM1, GM2 (SEQ ID NO: 3) and GM3 (SEQ ID NO: 4)). The transfected cells were treated with either DMSO as a solvent control or guanosine as the aptamer ligand. In the absence of guanosine treatment, cells transfected with construct MG1, GM1 or GM2 showed reduced luciferase expression in comparison with cells transfected with the control construct. Guanosine treatment of cells with MG1, GM1 or GM2, but not GM3, increased luciferase expression. Luciferase activity was expressed as mean±S.D. (n=3), and the induction fold was expressed as the quotient of luciferase activity obtained in the presence of guanosine divided by the value obtained in the absence of guanosine.

In another three constructs, GM1 (SEQ ID NO: 2), GM2 (SEQ ID NO: 3), and GM3 (SEQ ID NO: 4), the guanine aptamer was inserted upstream of mascRNA sequence (FIG. 3b). In the GM1 and GM2 constructs, a 7-nucleotide sequence (GM1) or a 6-nucleotide sequence (GM2) plus the first nucleotide in mascRNA (G) and their complementary sequences were inserted at 5' and 3' ends of guanine aptamer sequence respectively, and form the effector region stem of aptamer structure upon ligand binding. When the effector region stem is not formed in the absence of aptamer ligand, the 7 or 6-nucleotide sequence at the 3' end of guanine aptamer is single-stranded and serves as the leader sequence of mascRNA for RNase P cleavage. Upon aptamer/ligand binding, the leader sequence, as well as the first nucleotide in the acceptor stem of mascRNA, is sequestered in the stem of aptamer structure, therefore single stranded RNA would not be available for RNase P binding and subsequent cleavage. As shown in FIG. 3c, in the absence of guanosine, cells transfected with GM1 construct showed 52% reduction in luciferase activity comparing to Con8 control. Whereas in the presence of guanosine treatment, cells yielded nearly 100% luciferase activity of control construct, and generating 2.9-fold induction when comparing to cells without guanosine treatment. Cells transfected with construct GM2 had similar basal level luciferase activity as MG1, generating a 40% reduction in luciferase activity in the absence of guanosine, suggesting a similar efficiency in RNase P-mediated cleavage of mRNA. However, the induced luciferase activity was lower than MG1, generating a 1.9-fold induction of luciferase activity upon treatment of guanosine. In contrast, in construct GM3, there is 5-nt sequence between the effector region stem and the acceptor stem of the mascRNA. As shown in FIG. 3c, there is no increase in luciferase expression upon guanosine treatment, suggesting the RNase P cleavage was not affected by the ligand-bound aptamer structure.

These results demonstrate that aptamer-based riboswitches were generated that regulate target gene expression through modulating RNase P cleavage of mRNA in response to aptamer ligand.

Example 3

Figure 4A:
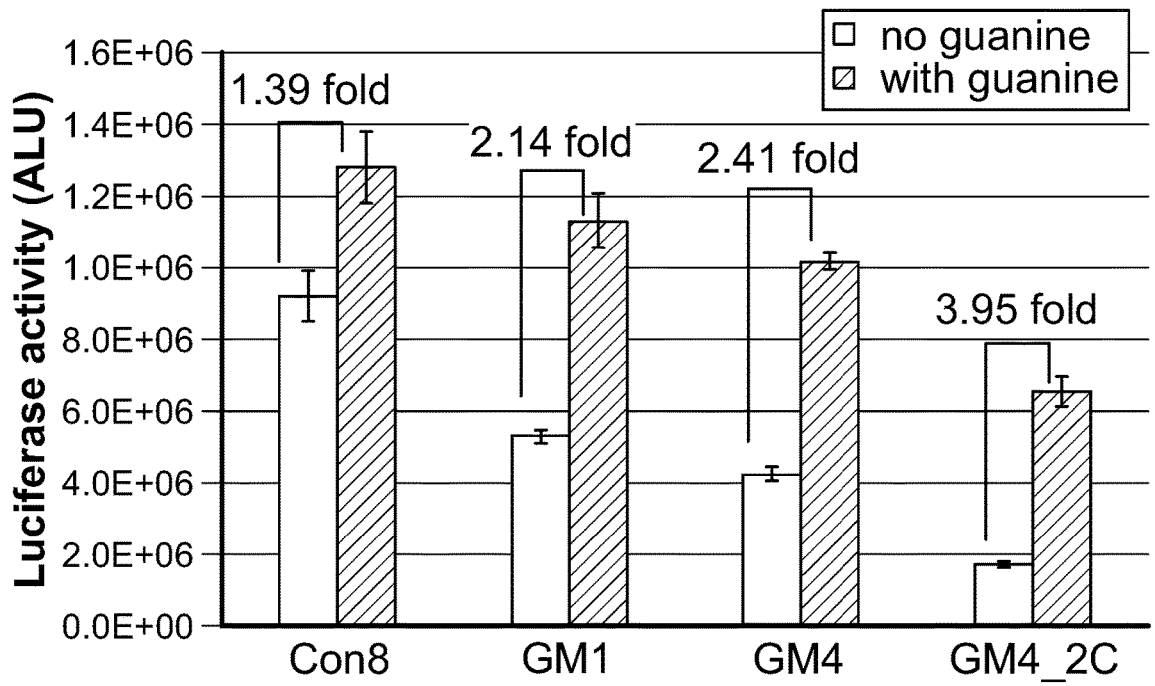
FIG. 4a. Change in local sequence upstream (5') of the aptamer stem affects riboswitch activity in the GM constructs. Luciferase activity was measured in HEK 293 cells transfected with the indicated constructs and treated with or without guanine. GM4 (SEQ ID NO: 5) has 3 nucleotide change from GM1 in which three nucleotides 5' of the aptamer stem are changed to reduce the potential for additional base paring by these nucleotides.

Local Sequence Around Aptamer Stem and the Distance Between Aptamer and tRNA-Like Structure Affect the Riboswitch Activity Results:

Experiments were performed to examine if the ligand-unbound aptamer structure could interfere with RNase P binding and cleavage when placed close to a tRNA-like structure. The sequences either downstream or upstream of the aptamer sequence could facilitate the effector region stem formation. In construct GM1, 4 nucleotides were mutated, namely CGGC that are at upstream of the effector region and could potentially base pair with sequence downstream of the effector region, to AAGA, generating construct GM4 (SEQ ID NO: 5). As shown in FIG. 4a, GM4 expressed lower level of luciferase activity than GM1, indicating a more efficient cleavage of mRNA in the absence of aptamer ligand guanine. When two copies of GM4 were inserted in tandem in the 3' UTR (GM4_2C, SEQ ID NO: 6), the basal level expression was further reduced to 18% of the control construct Con8. In the presence of guanine treatment, the luciferase expression was induced to 51% of the luciferase of Con8, generating 3.95-fold induction when compared to samples without guanine treatment.

Figure 4B:
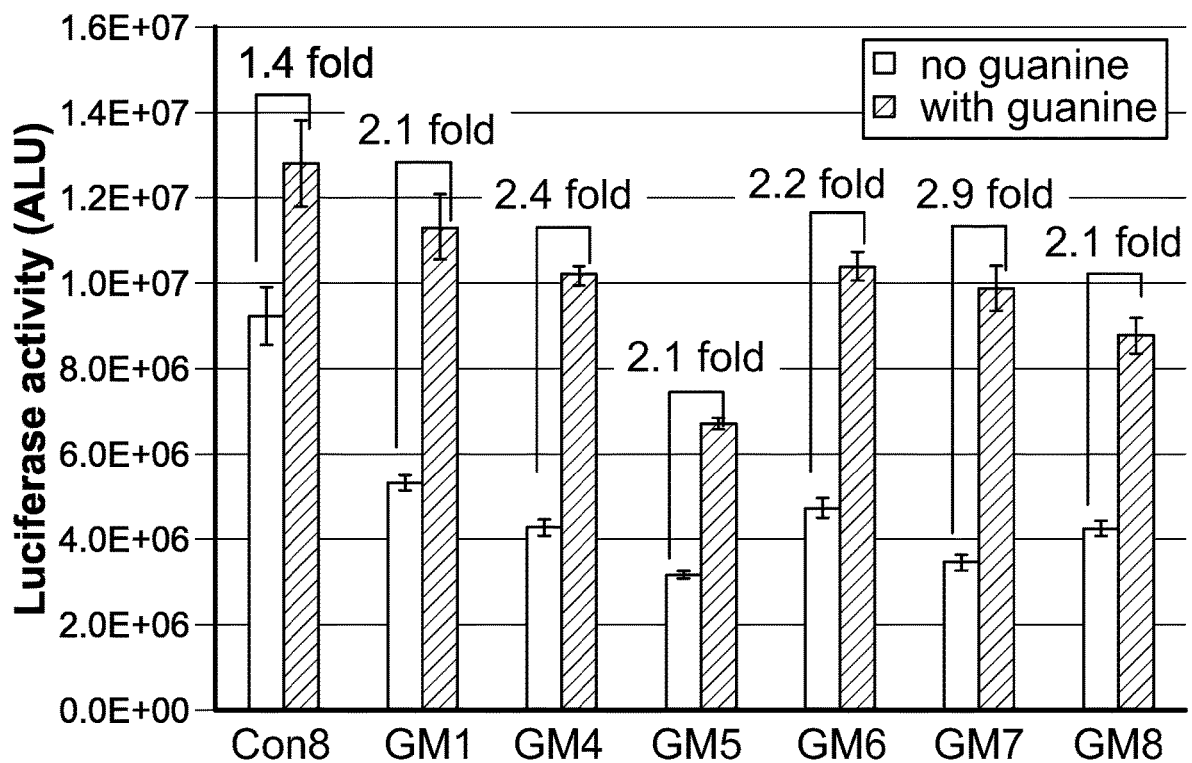
FIG. 4b. Distance between aptamer and RNase P substrate affects riboswitch activity in the GM constructs. The location of the aptamer/effector region in the GM constructs was moved upstream (5') in one nucleotide increments compared to the mascRNA allowing 0 to 3 nucleotides (constructs GM5 to GM8 (SEQ ID NO: 7-10), respectively) of leader sequence that is not part of the effector region (aptamer) stem. Luciferase activity, expressed as mean±S.D., was measured from HEK 293 cells transfected with the indicated constructs and treated with or without guanine and (n=3). The induction fold was expressed as the quotient of luciferase activity obtained in the presence of guanine divided by the value obtained in the absence of guanine. The GM5 construct, where there is no space between the two structures, has more efficient RNase P-mediated cleavage as indicated by the lower basal level of luciferase expression than construct GM4.

The sequence distance between aptamer structure and tRNA-like structure was also modified. As shown in FIG. 3c, construct GM3, in which there is 5 nucleotides between the effector stem of xpt-guanine aptamer riboswitch and the acceptor stem of the mascRNA, does not regulate luciferase gene expression in response to guanosine treatment, indicating conformational change in aptamer structure in response to ligand does not interfere with RNase P activity when placed 5 nucleotides away from tRNA-like structure. The number of nucleotides between the between the 3' end of the effector region stem and the acceptor stem of the mascRNA structure was modified starting from the GM4 construct (where the first nucleotide in the acceptor stem of mascRNA is involved in effector region stem formation of the riboswitch). Zero, 1, 2, or 3 nucleotides were inserted to generate construct GM5 to GM8 (SEQ ID NO: 7-10), respectively. As shown in FIG. 4b, construct GM5 expresses lower level of luciferase activity in the absence of guanine, indicating a more efficient cleavage by RNase P. However, further separating the two structures did not improve RNase P cleavage. Unlike, GM3 which has 5 nucleotides in between and has no regulation, GM6, 7 and 8 upregulate luciferase expression in response to guanine treatment.

Figure 4C:
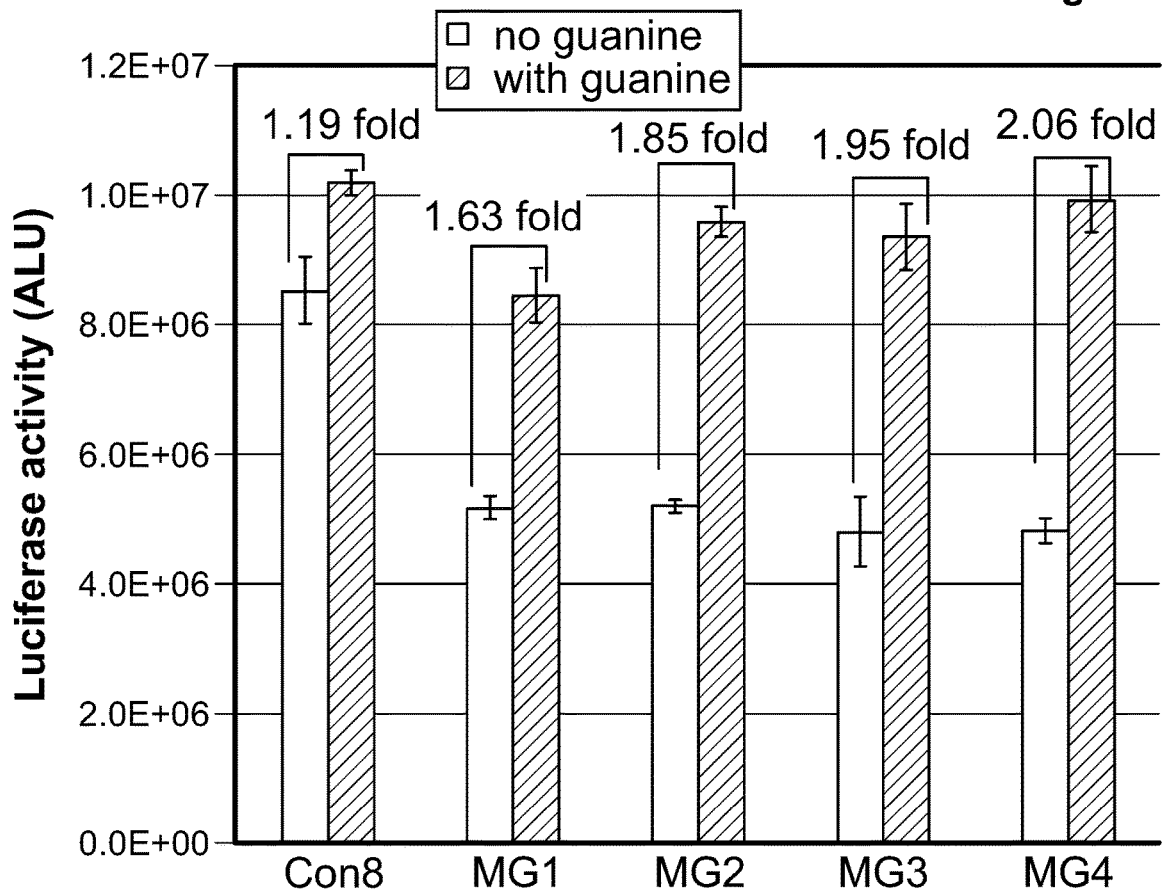
FIG. 4c. The effect of the length of the riboswitch effector region that is complementary to the acceptor stem of the RNase substrate in the MG constructs. Constructs MG1 to MG4 were created having an effector region stem with 6 to 3 nucleotides, respectively, that are complementary to the acceptor stem of the mascRNA (each with an effector region stem of 8 bp total). MG3 (SEQ ID NO: 12) and MG4 (SEQ ID NO: 13) have slightly more efficient RNase P cleavage than MG1, and more efficient induction of luciferase upon treated with guanine.

Similarly, the distance between the aptamer and RNase P substrate in the MG1 construct was modified by reducing the number of nucleotides that are alternatively shared between the acceptor stem of mascRNA and effector region stem, from 6 nucleotides in MG1 to 5, 4, or 3 nucleotides, generating the MG2, 3 and 4 (SEQ ID NO: 11-13, respectively) constructs, respectively (while retaining an effector region stem of 8 base pairs total). As shown in FIG. 4c, separating the two structures provides a modest decrease the basal level luciferase expression in the absence of guanine treatment when the alternatively shared nucleotides are reduced to 4 nucleotides (construct MG3) or 3 nucleotides (construct MG4), indicating a slightly more efficient RNase P-mediated mRNA cleavage. In the presence of guanine treatment, the luciferase expression was induced to the level that is comparable to MG1, generating approximately 2-fold induction for constructs MG3 and MG4. The alternatively shared nucleotides can be further reduced to 2 nucleotides or less to further separate the RNase P substrate structure and the aptamer structure to improve the regulatability of the riboswitch.

Example 4

Use of xpt-Guanine Aptamer to Regulate Target Gene Expression Through Modulating Pre-tRNA$^{Arg}$-RNase P-Mediated Cleavage of mRNA Experimental Procedure:

Plasmid construction: a DNA fragment containing sequences for the guanine aptamer xpt-G and human arginine pre-tRNA (Nashimoto M. N. et al. Long 5' leaders inhibit removal of a 3' trailer from a precursor tRNA by mammalian tRNA 3' processing endoribonuclease. Nucleic Acids Research, 1999; 27(13): 2770-2776) were synthesized (IDT). The synthesized DNA fragments were digested with BamHI and XhoI restriction enzymes and cloned into the Con8 construct digested with the same restriction enzymes. Construct sequences were verified by DNA sequencing (Genewiz).

Figure 5:
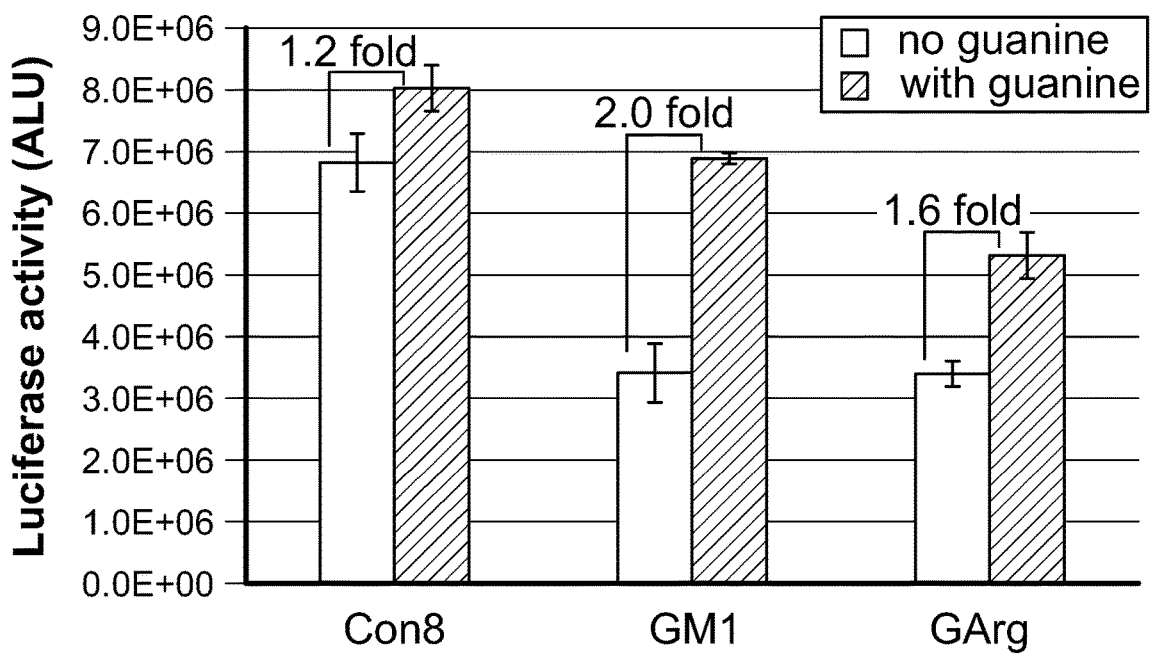
FIG. 5. Xpt-guanine aptamer modulated RNase P cleavage mediated through human tRNA$^{Arg}$ as the RNase P substrate. Luciferase activity was measured from HEK 293 cells transfected with control construct Con8, GM1 (containing mascRNA) or GArg (SEQ ID NO: 14) (containing human tRNA$^{Arg}$). The transfected cells were treated with or without guanine and the luciferase activity was measured and expressed as mean±S.D. (n=3). The induction fold was expressed as the quotient of luciferase activity obtained in the presence of guanine divided by the value obtained in the absence of guanine.

Results:

To further demonstrate the applicability of aptamer-mediated RNase P cleavage in regulating gene expression, human arginine tRNA sequence (tRNA$^{Arg}$) was linked to a xpt-guanine aptamer. In construct GM1, the mascRNA sequence was replaced with human arginine tRNA sequence. The 5' effector region stem sequence was designed to be complementary to 7 nucleotides of the tRNA$^{Arg}$ leader sequence plus the first nucleotide of the tRNA$^{Arg}$ acceptor stem, generating construct GArg (SEQ ID NO: 14). As shown in FIG. 5, in the absence of guanine, GArg expresses similar level of luciferase activity, approximately 50% of the control construct Con8, indicating a similar ability of tRNA$^{Arg}$ as mascRNA in recruiting RNase P-mediated cleavage. Guanine treatment induces 1.6-fold induction of luciferase when compared to the untreated samples, slightly less efficient than GM1 construct in response to guanine.

Example 5

Use of Theophylline Aptamer and Adenine Aptamer to Regulate Target Gene Expression Through Modulating mascRNA-RNase P-Mediated Cleavage of mRNA Experimental Procedure:

Plasmid construction: a DNA fragment containing sequences for the adenine aptamer ydhl-A (M. Mandal and R. R. Breaker, Adenine riboswitches and gene activation by disruption of a transcription terminator. Nature Structural & Molecular Biology. 2004; 11: 29-35, incorporated herein by reference) or theophylline aptamer (G. R. Zimmerman, et al. Interlocking structural motifs mediate molecular discrimination by a theophylline-binding RNA. Nature Structural Biology. 1997; 4: 644-649, incorporated herein by reference), and mascRNA sequence were synthesized (IDT). The synthesized DNA fragments were digested with BamHI and XhoI restriction enzymes and cloned into Con8 digested with the same restriction enzymes. Construct sequences were verified by DNA sequencing (Genewiz).

Transfection and Luciferase assay of cultured cells: as described in Example 1.

Four hours after transfection, the media was aspirated, and new media with NaOH (1 mM) as solvent or 1 mM adenine (Calbiochem), or 3 mM theophylline (Sigma) was added. The induction fold was expressed as the quotient of luciferase activity obtained in the presence of aptamer ligand divided by the value obtained in the absence of the aptamer ligand.

Figure 6A:
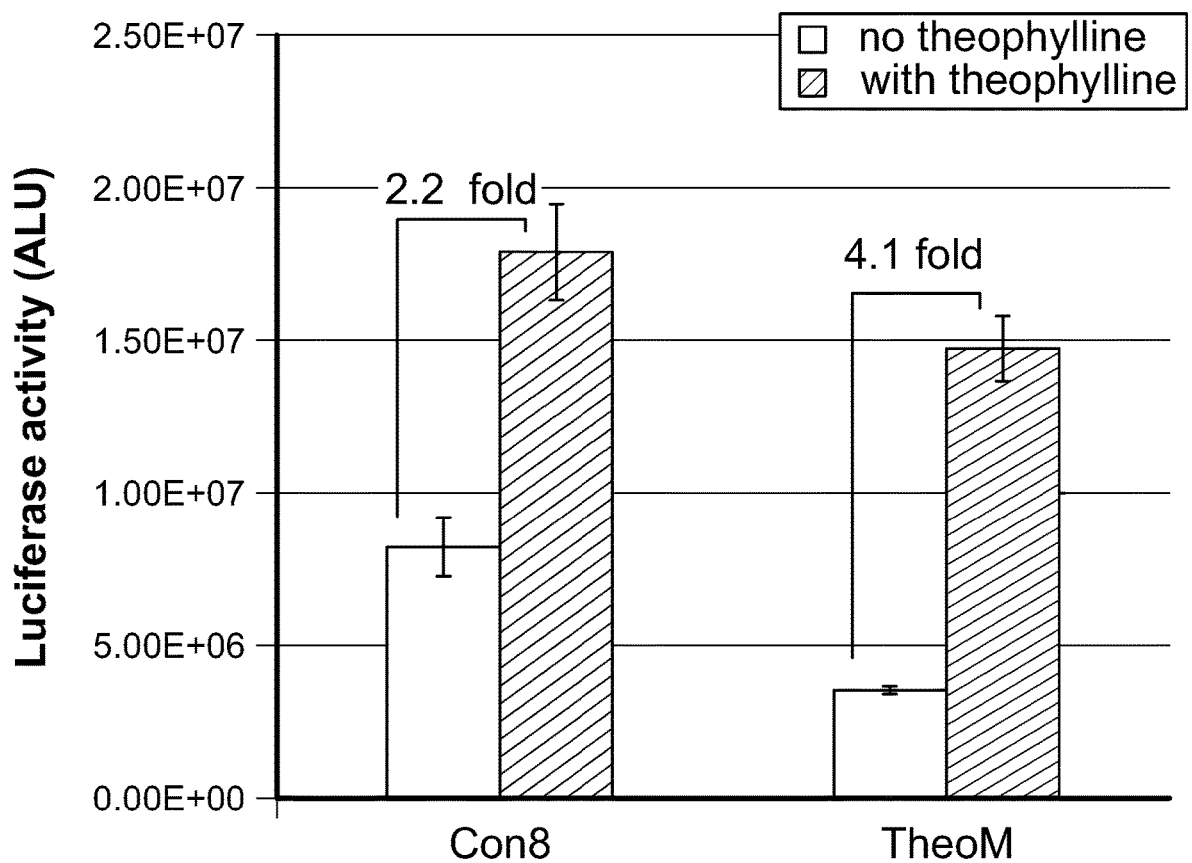
FIGS. 6a and 6b. Riboswitches with a theophylline aptamer or adenine aptamer modulated mascRNA-RNase P mediated mRNA cleavage. Luciferase activity was measured from HEK 293 cells transfected with control construct Con8, construct TheoM (SEQ ID NO: 16), containing theophylline aptamer and mascRNA (FIG. 6a), or construct YM (SEQ ID NO: 15) containing ydhl-A adenine aptamer and mascRNA (FIG. 6b). The transfected cells were treated with or without 3 mM theophylline or 1 mM adenine, and the luciferase activity was measured and expressed as mean±S.D. (n=3). The induction fold was expressed as the quotient of luciferase activity obtained in the presence of aptamer ligand divided by the value obtained in the absence of aptamer ligand.
Figure 6B:
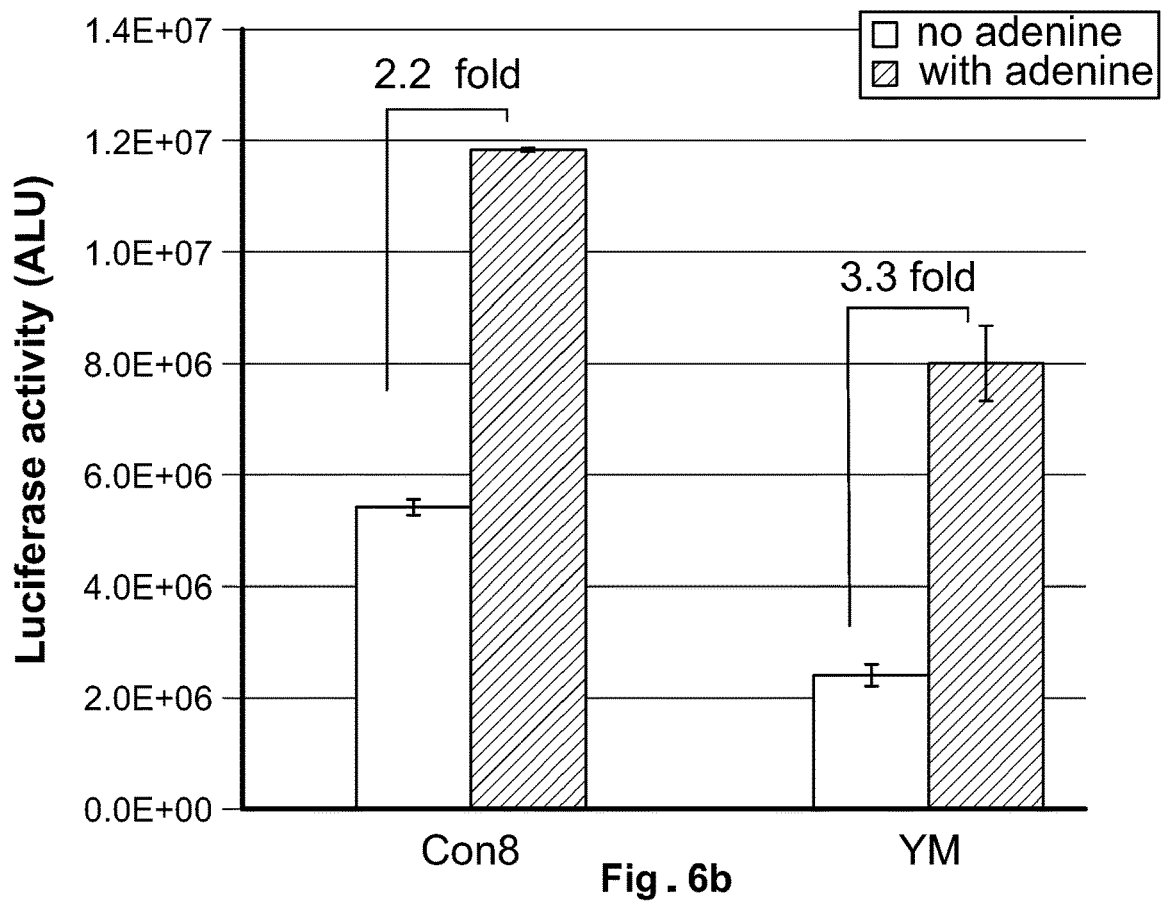

Results:

Use of additional aptamer/ligand pairs to control target gene expression were studied. Using the same strategy as in Example 2 for construct GM1, the xpt-guanine aptamer was replaced with either theophylline aptamer or ydhl-A adenine aptamer, generating the TheoM (SEQ ID NO: 16) and YM (SEQ ID NO: 15) constructs, respectively. As shown in FIG. 6a, in the absence of theophylline treatment, the TheoM construct expressed reduced level of luciferase, approximately 43.4% of the control Con8 construct, indicating the RNase P-mediated cleavage of mRNA. In the presence of theophylline treatment, the control construct expressed 2-fold increase in luciferase activity, through an aptamer-unrelated mechanism. However, the TheoM construct generated 4.1-fold increase in luciferase expression, indicating a theophylline/aptamer specific effect. Similarly, for construct YM, as shown in FIG. 6b, Adenine treatment increased luciferase activity by 2.2-fold in the control construct through an aptamer-unrelated mechanism. However, the YM construct generated 3.3-fold increase in luciferase expression, indicating an adenine/aptamer specific effect.

Example 6

Combined Use of RNase P Cleavage-Based Riboswitch and a Second Riboswitch to Obtain More Stringent Regulation of Target Gene Expression Experimental Procedure:

The G15 or G17 riboswitch cassette or a control cassette without aptamer was developed previously (see Examples 5 and 8 and SEQ ID NO.: 46 and 15 of WO 2016/126747, incorporated herein by reference). To generate construct GM1-G15 or GM1-G17, the fragment containing the guanine aptamer and mascRNA sequences was released from GM1 construct by BamHI and XhoI digestion and cloned into G15 or G17 construct digested with the same restriction enzymes. The regulation cassette G17_2IR3 (see SEQ ID NO.: 31 of WO 2016/126747, incorporated herein by reference) was cloned at the position 308 in the mouse erythropoietin cDNA using Golden Gate cloning strategy to generate Epo-G17_2IR3. The fragment containing the guanine aptamer and mascRNA sequences was released from GM1 construct by BamHI and XhoI digestion and cloned into Epo-G17_2IR3 digested with the same restriction enzymes to generate construct Epo-GM1-G17_2IR3.

ELISA for mouse erythropoietin: Transfection was as described in Example 1. Transfected HEK 293 cells were treated with or without 500 µM guanine. The supernatants from the transfected cells were collected 20 hours after ligand treatment and were subjected to ELISA. The ELISA was performed according to the manufacturer's instruction (R&D).

Results:

The expression constructs containing the GM1 through 8 riboswitches have a substantial level of basal expression of the target gene. Further, a previously-developed alternative splicing based riboswitch also has some degree of basal expression. A combined use of these switches in tandem can potentially tighten the basal expression and therefore generate more stringent regulation of target gene expression.

Figure 7A:
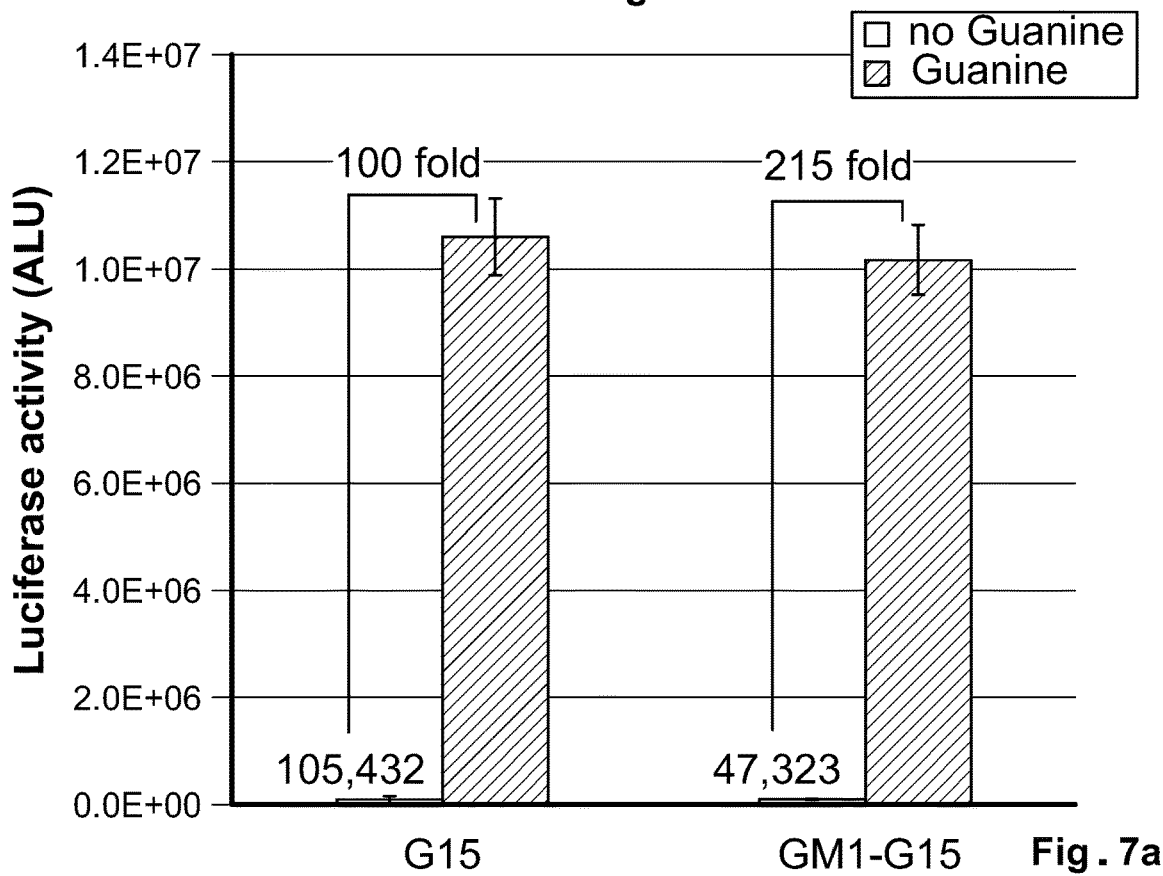
FIGS. 7a and 7b. Combined use of an RNase P substrate-based riboswitch with a second riboswitch to achieve more stringent regulation of target gene expression. Luciferase activity was measured from HEK 293 cells transfected with construct G15 or GM1-G15 (FIG. 7a), or construct G17 or GM1-G17 (FIG. 7b). The transfected cells were treated with or without 500 µM guanine, and the luciferase activity was measured and expressed as mean±S.D. (n=3). The induction fold was expressed as the quotient of luciferase activity obtained in the presence of guanine divided by the value obtained in the absence of guanine.
Figure 7B:
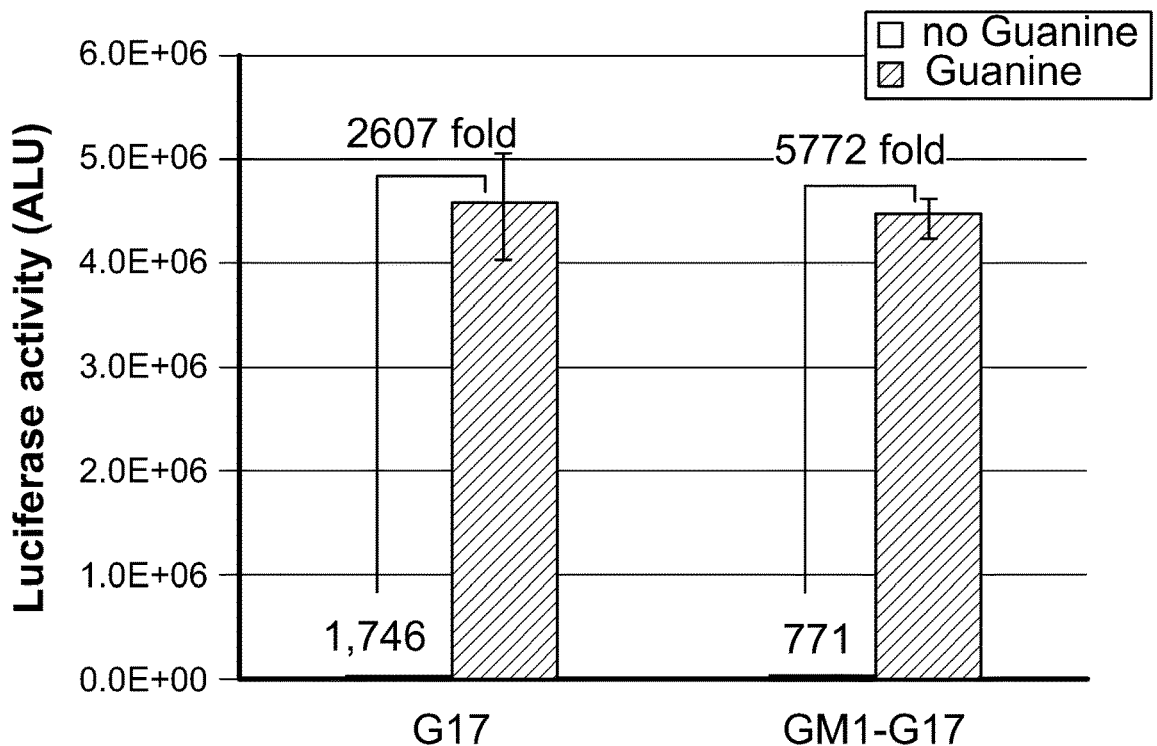
Figure 7C:
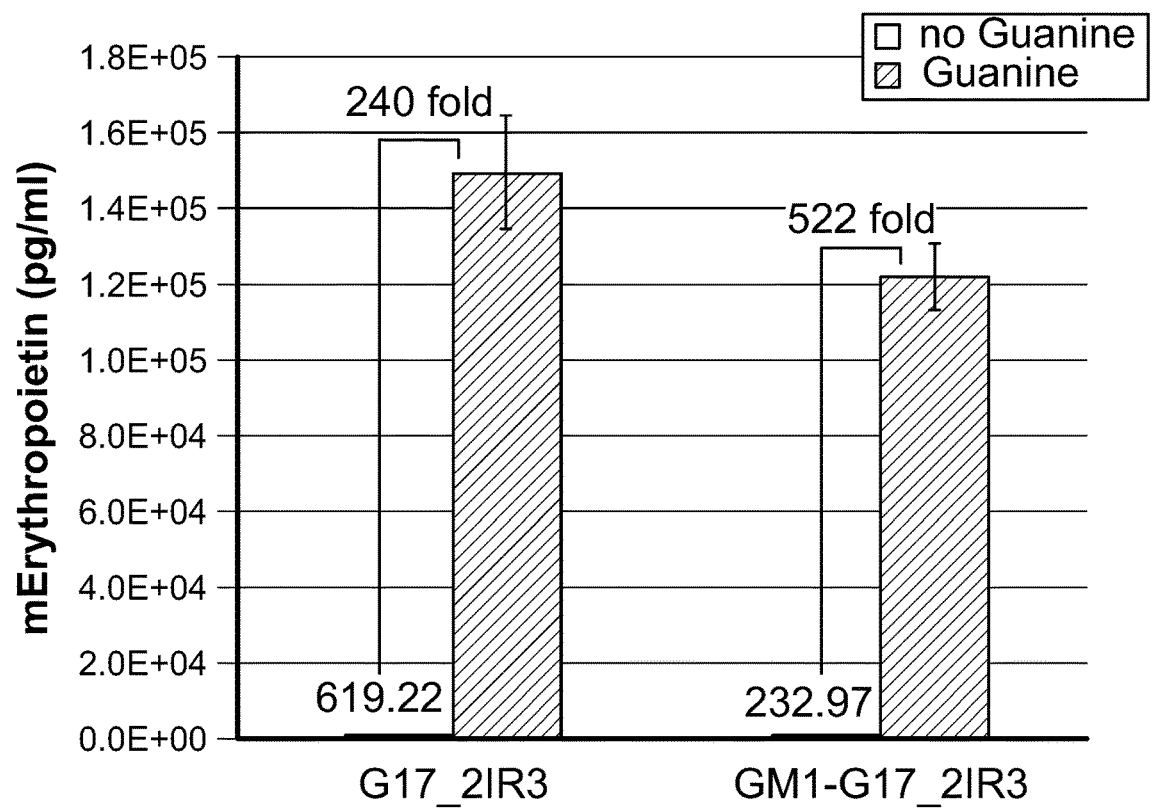
FIG. 7c. Combined use of RNase P substrate-based riboswitch with a second riboswitch to achieve more stringent regulation of Epo target gene expression. Expression of mouse Epo protein was measured using ELISA from supernatants collected from HEK 293 cells transfected with construct G17_2IR3 or construct GM1-G17_2IR3. The concentration of Epo was expressed as mean±S.D. (n=3), and the induction fold was expressed as the quotient of the concentration of Epo obtained in the presence of guanine divided by the concentration of Epo obtained in the absence of guanine.

To demonstrate this, the G15 riboswitch was combined with the tRNA-RNase P-based riboswitch. G15 riboswitch is based on xpt-guanine aptamer-modulated alternative splicing mechanism and has some degree of basal level expression, that reduces the fold induction in response to aptamer ligand guanine treatment. To reduce the basal level expression from G15 construct, the 3'UTR was replaced with that from GM1 construct, generating construct GM1-G15 that contains two riboswitches. As shown in FIG. 7a, in the absence of aptamer ligand (guanine), the basal level expression of luciferase of GM1-G15 is substantially reduced to approximately 45% of the luciferase activity from G15. In the presence of guanine treatment, the induced level of luciferase activity from GM1-G15 is 96% of the G15 but the fold induction is higher than G15 (215 fold v.s. 100 fold), due to the reduced basal level expression. Similar strategy was used to generate construct GM1-G17, in which G17 has much lower basal level expression than G15. Combining G17 with GM1 further reduced the basal level target gene expression and generate higher induction fold of target gene expression in response to guanine treatment, as shown in FIG. 7b. Similar results were obtained when GM1 switch was combined with G17_2IR3 to regulate the expression of mouse erythropoietin protein, as demonstrated in FIG. 7c.

These results demonstrate that a more stringent switch can be generated by combining in tandem two switches that have basal level expression. The aptamers in this dual switch can be the same or different aptamers that bind to the same or different ligands as demonstrated here, or aptamers responding to different ligands.

I claim:

1. A polynucleotide cassette for the regulation of the expression of a target gene the cassette encoding an RNase P substrate sequence linked to a riboswitch, wherein:
   the RNase P substrate sequence comprises a sequence encoding a tRNA, mascRNA, MEN beta tRNA-like structure, or a viral tRNA-like structure—that can initiate RNase P cleavage; wherein the RNase P substrate sequence comprises a leader sequence and an acceptor stem;
   the riboswitch is recombinant and comprises an effector region linked to an aptamer sequence;
   the aptamer can specifically bind a small molecule ligand;
   the aptamer undergoes a conformational change when it binds the small molecule ligand;
   the effector region comprises sequence complementary to a portion of the RNase P substrate sequence, the portion comprising leader sequence and/or acceptor stem sequence; and
   the effector region sequence is linked to the aptamer such that the conformational change in the aptamer results in formation of a stem comprising the RNase P substrate sequence and the portion of the effector region complementary thereto, wherein the stem can inhibit cleavage of the substrate by RNase P.

2. The polynucleotide cassette of claim 1, wherein the stem comprising the RNase P substrate sequence and the portion of the effector region complementary thereto comprises 6 to 12 base pairs.

3. The polynucleotide cassette according to claim 1, wherein the aptamer sequence is located 5' to the RNase P substrate sequence and the effector region comprises sequence complementary to the leader sequence of the RNase P substrate.

4. The polynucleotide cassette of claim 3, wherein the acceptor stem of the RNase P substrate and the riboswitch effector region are separated by 0, 1, 2, 3, or 4 nucleotides.

5. The polynucleotide cassette of claim 3, wherein the effector region additionally comprises sequence complementary to the 5' arm of the acceptor stem of the RNase P substrate sequence.

6. The polynucleotide cassette according to claim 1, wherein the aptamer sequence is located 3' to the RNase P substrate sequence and the effector region comprises sequence complementary to the 3' arm of the acceptor stem of the RNase P substrate sequence.

7. The polynucleotide cassette of claim 6, wherein the effector region sequence complementary to the 3' arm of the acceptor stem of the RNase P substrate is 1 to 7 nucleotides.

8. A method of modulating the expression of a target gene comprising:
   a. inserting the polynucleotide cassette of claim 1 into an untranslated region (UTR) of the target gene,
   b. introducing the target gene comprising the polynucleotide cassette into a cell, and
   c. exposing the cell to a small molecule ligand that specifically binds the aptamer in an amount effective to increase expression of the target gene.

9. The method of claim 8, wherein the aptamer sequence of the polynucleotide cassette is located 5' to the RNase P substrate sequence and the effector region comprises sequence complementary to the leader sequence of the RNase P substrate.

10. The method of claim 9, wherein the acceptor stem of the RNase P substrate and the riboswitch effector region are separated by 0, 1, 2, 3, or 4 nucleotides.

11. The method of claim 8, wherein the aptamer sequence of the polynucleotide cassette is located 3' to the RNase P substrate sequence and the effector region comprises sequence complementary to the 3' arm of the acceptor stem of the RNase P substrate sequence.

12. The method of claim 11, wherein the effector region sequence that is complementary to the 3' arm of the acceptor stem of the RNase P substrate is 1 to 7 nucleotides.

13. The method of claim 8, wherein the polynucleotide cassette is inserted into the 5' untranslated region of the target gene.

14. The method of claim 8, wherein the polynucleotide cassette is inserted into the 3' untranslated region of the target gene.

15. The method of claim 8, wherein two or more of the polynucleotide cassettes are inserted into the target gene.

16. The method of claim 15, wherein the two or more polynucleotide cassettes comprise different aptamers that specifically bind to different small molecule ligands.

17. The method of claim 15, wherein the two or more polynucleotide cassettes comprise the same aptamer.

18. The method of claim 8, wherein the target gene further comprises a gene regulation cassette that modulates target gene expression by aptamer-mediated regulation of alternative splicing.

19. The method of claim 8, wherein the target gene comprising the polynucleotide cassette is incorporated in a vector for the expression of the target gene.

20. The method of claim 19, wherein the vector is a viral vector.

21. The method of claim 20, wherein the viral vector is selected from the group consisting of adenoviral vector, adeno-associated virus vector, and lentiviral vector.

22. A vector comprising a target gene that contains a polynucleotide cassette according to claim 1.

23. The vector of claim 22, wherein the vector is a viral vector.

24. The vector of claim 23, wherein the viral vector is selected from the group consisting of adenoviral vector, adeno-associated virus vector, and lentiviral vector.

25. The vector of claim 22, wherein the target gene further comprises a gene regulation cassette that modulates target gene expression by aptamer-mediated regulation of alternative splicing.

* * * * *